(12) United States Patent
Makaram et al.

(10) Patent No.: US 11,287,405 B2
(45) Date of Patent: Mar. 29, 2022

(54) GAS SENSING SYSTEMS AND METHODS OF OPERATION THEREOF

(71) Applicant: Infineon Technologies AG, Neubiberg (DE)

(72) Inventors: Prashanth Makaram, Berlin (DE); Abidin Güçlü Onaran, Munich (DE)

(73) Assignee: INFINEON TECHNOLOGIES AG, Neubiberg (DE)

(*) Notice: Subject to any disclaimer, the term of this patent is extended or adjusted under 35 U.S.C. 154(b) by 50 days.

(21) Appl. No.: 16/852,035

(22) Filed: Apr. 17, 2020

(65) Prior Publication Data
US 2020/0319153 A1 Oct. 8, 2020

Related U.S. Application Data

(62) Division of application No. 15/663,711, filed on Jul. 29, 2017, now Pat. No. 10,677,768.

(51) Int. Cl.
*G01N 33/00* (2006.01)
*G01N 27/04* (2006.01)
(Continued)

(52) U.S. Cl.
CPC .......... *G01N 33/0008* (2013.01); *G01N 27/04* (2013.01); *G01N 27/12* (2013.01);
(Continued)

(58) Field of Classification Search
CPC ....... G01N 33/0008; G01N 2033/0068; G01N 27/12; G01N 33/0006; G01N 27/04; G01N 27/16; Y10S 435/807
See application file for complete search history.

(56) References Cited

U.S. PATENT DOCUMENTS 5,347,474 A 9/1994 Wong
5,716,506 A * 2/1998 Maclay ................ G01N 27/404
204/424
(Continued)

FOREIGN PATENT DOCUMENTS

CN 102778538 A 11/2012

OTHER PUBLICATIONS

Tsukada et al., "Dual-Gate Field-Effect Transistor Hydrogen Gas Sensor with Thermal Compensation" Japanese Journal of Applied Physics 49 (2010) 024206 (Year: 2010).*

(Continued)

*Primary Examiner* — John C Kuan
(74) *Attorney, Agent, or Firm* — Slater Matsil, LLP

(57) ABSTRACT

A sensor device includes a gas sensor disposed on a first substrate, a heating element disposed within the first substrate, a processor operatively coupled to the gas sensor and the heating element, and a memory storing a program to be executed by the processor. The gas sensor is configured to measure first sensor data points and second sensor data points. The gas sensor overlaps the heating element. The program includes instructions for performing the following steps in real-time: recording first resistance values and second resistance values of the heating element; adjusting the second sensor data points using the first sensor data points, the first resistance values, and the second resistance values to obtain corrected sensor data points; and determining sensed values from the corrected sensor data points.

20 Claims, 15 Drawing Sheets

(51) Int. Cl.
*G01N 27/12* (2006.01)
*G01N 27/16* (2006.01)

(52) U.S. Cl.
CPC ......... *G01N 27/16* (2013.01); *G01N 33/0006* (2013.01); *G01N 2033/0068* (2013.01); *Y10S 435/807* (2013.01)

(56) References Cited

U.S. PATENT DOCUMENTS

| | | |
|---|---|---|
| 10,295,457 B1* | 5/2019 | Ocheltree ............ G01N 21/274 |
| 2002/0092779 A1 | 7/2002 | Essalik et al. |
| 2006/0155486 A1 | 7/2006 | Walsh et al. |
| 2006/0173637 A1 | 8/2006 | Martin |
| 2011/0218414 A1 | 9/2011 | Kamath et al. |
| 2013/0018599 A1 | 1/2013 | Peng |
| 2013/0056703 A1* | 3/2013 | Elian ....................... H01L 24/49 |
| | | 257/9 |
| 2014/0238100 A1 | 8/2014 | Londergan et al. |
| 2014/0260545 A1 | 9/2014 | Ruhl et al. |
| 2014/0260547 A1 | 9/2014 | Balandin |
| 2016/0238578 A1* | 8/2016 | Lakhotia ................ G01N 27/12 |
| 2018/0195947 A1 | 7/2018 | Andoh |

OTHER PUBLICATIONS

Hossein-Babaei, F. et al., "Compensation for the drift-like terms caused by environmental fluctuations in the responses of chemoresistive gas sensors," Sensors and Actuators B: Chemical, 143 (2010) 641-648, Year: 2010, 8 pages.

* cited by examiner

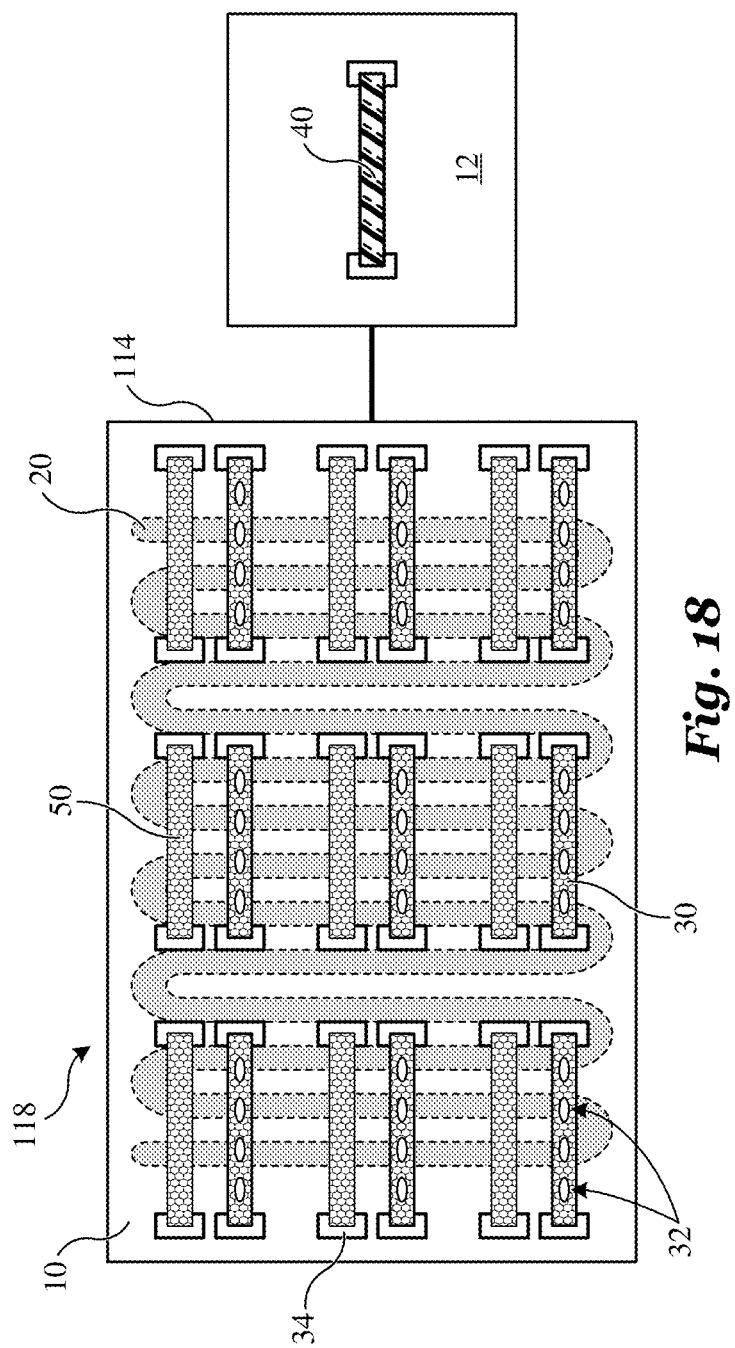

GAS SENSING SYSTEMS AND METHODS OF OPERATION THEREOF

CROSS-REFERENCE TO RELATED APPLICATIONS

This application is a divisional application of U.S. patent application Ser. No. 15/663,711, filed on Jul. 29, 2017, which application is hereby incorporated herein by reference in its entirety.

TECHNICAL FIELD

The present invention relates generally to a sensing system, and, in particular embodiments, to gas sensing system structures and the methods of operation thereof.

BACKGROUND

Sensing systems including sensor devices such as resistive gas sensors can detect the presence of target analytes in an ambient environment. It may be important to design sensor devices with the ability to output detection events in real-time with high sensitivity. Sensor devices may also be designed for high accuracy and specificity with respect to a target analyte or group of target analytes. In the specific case of resistive gas sensors, detection events may be based on the change in resistance or capacitance of a semiconducting thin-film structure that is influenced by the adsorption of gas molecules.

As the sensitivity of a sensor device improves, the influence of external environmental factors on the sensor device may also increase. Such environmental factors may include temperature, humidity, composition and concentration of species in the ambient atmosphere, and electromagnetic interference, among others. High sensitivity to external environmental factors may decrease sensor accuracy. Therefore, sensor devices which compensate for external environmental influences may be desirable in order to provide both high sensitivity and high accuracy.

SUMMARY

In accordance with an embodiment of the invention, a method of sensing includes obtaining first sensor data points by a sensor, obtaining first reference data points, and determining a correlation between the first sensor data points and the first reference data points. The method of sensing further includes measuring second sensor data points by the sensor, obtaining second reference data points, and adjusting the second sensor data points using the correlation and the second reference data points to obtain corrected sensor data points. The method of sensing also includes determining sensed values from the corrected sensor data points and storing the sensed values.

In accordance with another embodiment of the invention, a method of sensing includes obtaining first sensor data points by a sensor and obtaining first reference data points. Obtaining the first sensor data points and the first reference data points is performed during a first time interval. The method of sensing further includes measuring second sensor data points by the sensor and generating corrected second sensor data points by correcting for baseline variation in the second sensor data points using a relationship between the first sensor data points and the first reference data points. The measuring the second sensor data points and generating the corrected second sensor data points is performed after the first time interval during a second time interval. The method of sensing also includes determining sensed values from the corrected second sensor data points.

In accordance with still another embodiment of the invention, a sensor device includes a gas sensor disposed on a first substrate. The gas sensor is configured to measure first sensor data points and second sensor data points. A heating element is disposed within the first substrate. The gas sensor overlaps the heating element. A processor is operatively coupled to the gas sensor and the heating element. The sensor device also includes a memory storing a program to be executed by the processor. The program includes instructions for recording first resistance values and second resistance values of the heating element. The program also includes instructions for adjusting the second sensor data points using the first sensor data points, the first resistance values, and the second resistance values to obtain corrected sensor data points. The program further includes instructions for determining sensed values from the corrected sensor data points.

BRIEF DESCRIPTION OF THE DRAWINGS

For a more complete understanding of the present invention, and the advantages thereof, reference is now made to the following descriptions taken in conjunction with the accompanying drawings, in which:

FIG. 1A illustrates the method of sensing and FIG. 1B illustrates the sensing system;

FIG. 18 illustrates a top view of an example sensor device including multiple pairs of a sensor and a reference sensor and further including an environmental sensor where the environmental sensor is located on a second substrate in accordance with an embodiment of the invention;

FIG. 19A illustrates resistance responses of a sensor and a heating element before correcting the baseline variation and FIG. 19B illustrates resistance responses of the sensor and the heating element after correcting the baseline variation; FIG. 20A illustrates resistance responses of a sensor before correcting the baseline variation and FIG. 20B illustrates resistance responses of the sensor after correcting the baseline variation.

Figure 1A:
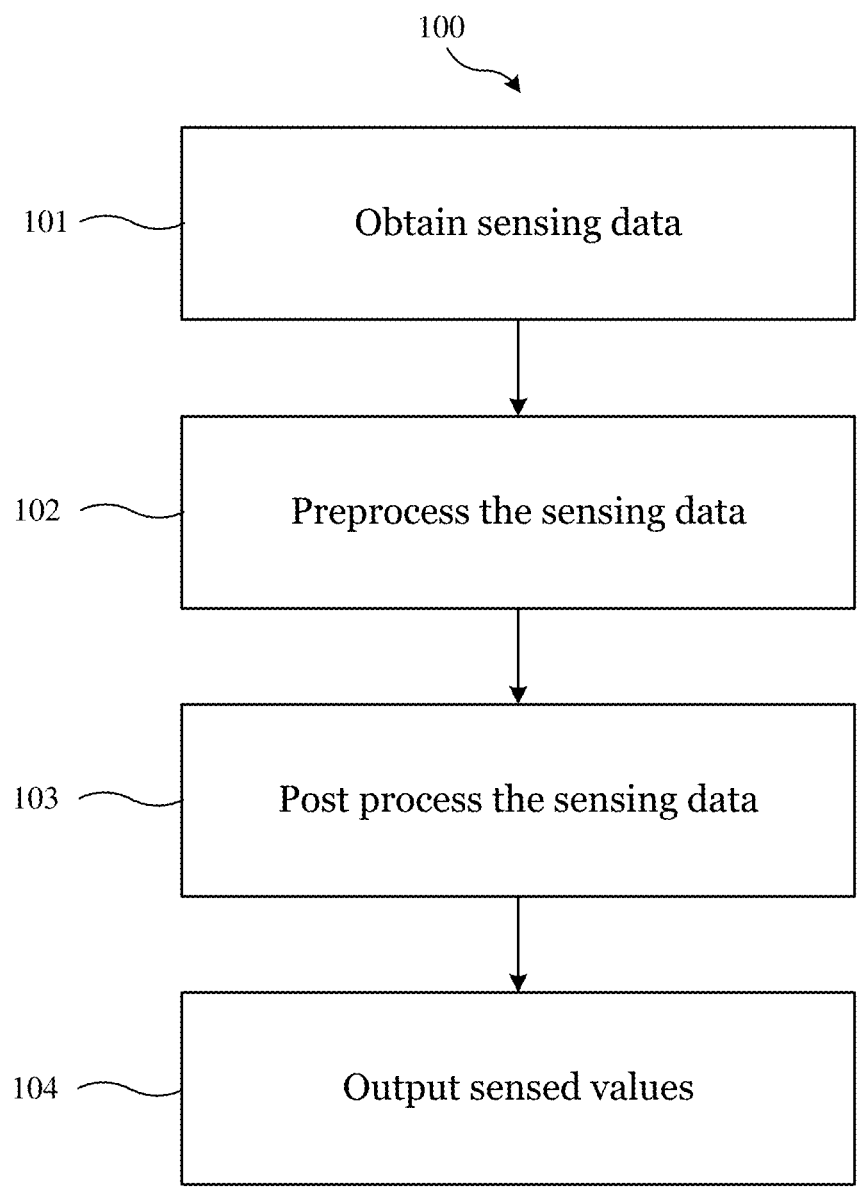
FIGS. 1A and 1B illustrate a method of sensing and a sensing system in accordance with an embodiment of the invention where

Corresponding numerals and symbols in the different figures generally refer to corresponding parts unless otherwise indicated. The figures are drawn to clearly illustrate the relevant aspects of the embodiments and are not necessarily drawn to scale. The edges of features drawn in the figures do not necessarily indicate the termination of the extent of the feature.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Sensing systems may be designed to detect quantities of a target analyte by determining the deviation of a measured value from a baseline value. For example, in a gas sensing system, electrical resistance of a sensor may be used as a measured value to detect target gases. In this system, the baseline or reference resistance may be on the order of 1 k$\Omega$, for example, when no target gases are present. Target gases may then be sensed by evaluating deviations of the sensor resistance from the value of 1 k$\Omega$. However, external factors that are unrelated to the target gas such as environmental factors may affect the sensor. These external factors may cause the baseline value to vary over time which may negatively impact the accuracy of the sensing system. Therefore, a sensing system that corrects for baseline variation may be advantageous.

In various embodiments, a sensing system is implemented that includes a sensor device configured to correct for baseline variation by processing sensing data according to an algorithm to correlate sensor output with reference measurements. The algorithm may include the steps of obtaining sensor data points and reference data points, determining a correlation between the sensor data points and the reference data points, and adjusting the sensor data points to correct for baseline variation. The sensor device may be a gas sensor in various embodiments and is a graphene-based resistive gas sensor in one embodiment. The baseline variation may be caused by environmental factors such as temperature and/or humidity.

The sensor device may advantageously enable higher sensitivity by correcting for baseline variation caused by external environmental factors. Such baseline variation may be a time-varying change in the baseline of a sensor and may be referred to as sensor drift in some implementations. The contribution to the signal caused by baseline variation may be diminished or removed entirely in various embodiments which may advantageously enable higher sensitivity to target analytes. In the specific case of a gas sensor device, the correction of baseline variation may beneficially enable accurate detection of low concentrations of gas molecules on the scale of parts-per-million (ppm), parts-per-billion (ppb), or lower.

The sensor device may also have the benefit of correcting for baseline variation without requiring that the sensor device operate at a specific temperature value. For example, the sensor device may operate at any temperature and baseline variation due to temperature fluctuation may be corrected. Another possible benefit of the sensor device may be that materials that are sensitive to environmental factors such as graphene may be used in the structure of the sensor device. In contrast, a conventional sensor device without correction for baseline variation may be designed to be very insensitive to the environment which may limit possible materials, structure, and performance of the conventional sensor device.

The sensor device may also advantageously perform adaptive corrections for baseline variation. Adaptive correction may include correlating changes in the baseline with the cause of baseline variation in real-time or near-real-time which may result in more accurate correction for baseline variation. For example, the effects of the environment on the baseline of a sensor device may vary over time and may not be known prior to the sensing events. Adaptive corrections for baseline variation may determine correlations immediately before performing corrections which may improve accuracy of the corrections as well as being applicable to many different sensing environments.

Embodiments provided below describe various structures and methods of operating sensing systems, and in particular, sensing systems that compensate for baseline variation. The following description describes the embodiments. Several embodiment methods of sensing are described using FIGS. 1-3. Two embodiment methods of preprocessing data are described using FIGS. 4 and 5. An embodiment method of adjusting a baseline and normalizing data points is described using FIG. 6. Various embodiment sensor devices which may be included in sensing system implementations are described using FIGS. 7-18. Qualitative graphs of two baseline correction scenarios are described using FIGS. 19 and 20.

Figure 1B:
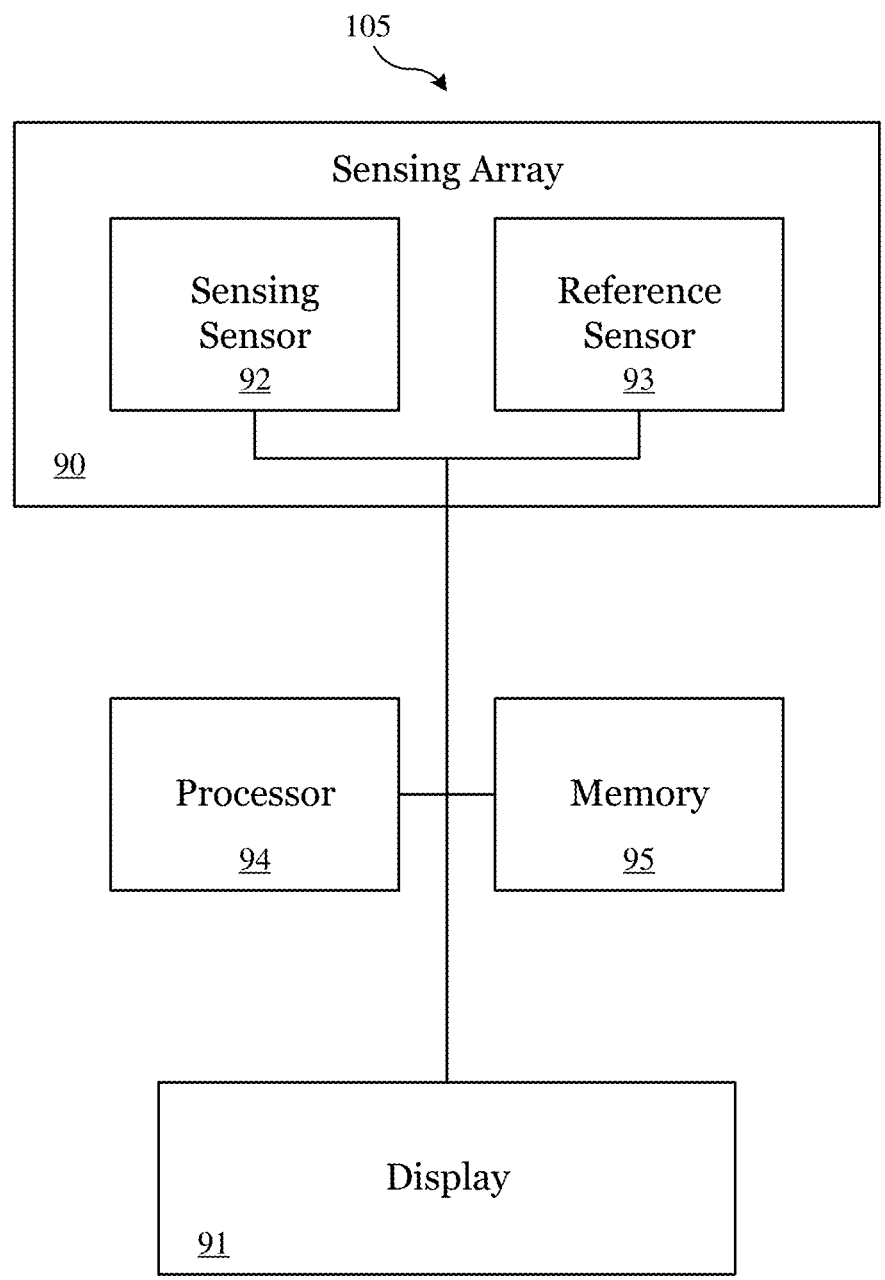

FIGS. 1A and 1B illustrate a method of sensing and a sensing system in accordance with an embodiment of the invention where FIG. 1A illustrates the method of sensing and FIG. 1B illustrates the sensing system.

Referring to FIGS. 1A and 1B, a method 100 of sensing includes the following steps which may be performed by a sensing system 105. Step 101 includes obtaining sensing data and may be performed by a sensing array 90. The step of obtaining sensing data may take various forms ranging from recording a single data point at an instant in time from a single sensor to recording multiple data points from a sensor array over a period time. For example, in one embodiment, step 101 includes obtaining sensing data by recording a single data point from a sensor and recording a single reference point from a reference sensor at an instant in time. In another embodiment, step 101 includes obtaining sensing data by recording four data points per second from each sensor in a sensor array and also from an environmental sensor over a period of ten seconds. Other variations may be apparent to those of ordinary skill in the art and may depend on a specific implementation of a sensor device.

The sensing array 90 may include only a single sensor or may include multiple sensors and types of sensors. For example, as shown in FIG. 1B, sensor array 90 includes a sensing sensor 92 and a reference sensor 93. In various embodiments, the reference sensor 93 may be used to determine appropriate baseline values for sensing sensor 92.

Step 102 includes preprocessing the sensing data. The step of preprocessing the sensing data may include processing steps that prepare the sensing data to be interpreted as sensing events. For example, if a sensor device includes multiple sensors in a sensor array, an averaging step may be performed while preprocessing the sensing data. As another example, preprocessing the sensor data may include detecting and removing outliers in the sensing data. Other possible preprocessing steps may include determining a baseline, correcting a baseline, normalizing data points, combining multiple types of data points, multiplying by scalar factors, removing data points from the beginning or end of a data set, and the like.

Step 103 includes post processing the sensing data. For example, the sensing data may include sensing events in the form of peaks or other identifiable features. The sensing events may be identified using criteria specific to the sensor implementation and sensed values may be determined from the sensing events. The processing steps 102 and 103 may be performed locally by a processor within a sensor device such as an application-specific integrated circuit (ASIC), a field-programmable gate array (FPGA), or a general purpose processor coupled to a memory storing a program, as examples. Alternatively, steps 102 and 103 may be performed externally by a computer that is connected to the sensor device such as a desktop computer, laptop computer, server, tablet computer, smart phone, and the like.

Steps 102 and 103 may be performed by a processor 94. The processor may be operatively coupled to sensing array 90 as well as a memory 95. In various embodiments, memory 95 may be used to store information obtained by preprocessing and post processing the sensing data. Memory 95 may also be used to store computer instructions that, when executed by processor 94, may perform steps 102 and 103 among others. Memory 95 may be a non-volatile computer-readable storage medium such as a computer hard drive, random access memory, and the like.

Step 104 includes outputting the sensed values in a format understandable by a user or a connected device. Step 104 may be performed by a display 91 operatively coupled to sensing array 90, processor 94, and memory 95. For example, the sensed values may be output to a digital display or formatted in a data file and stored on a computer-readable storage medium. In the specific case of a gas sensor, the sensed values may be output as a concentration such as parts-per-million (ppm) or parts-per-billion (ppb) to communicate a concentration of a sensed gas in an ambient environment.

Figure 2:
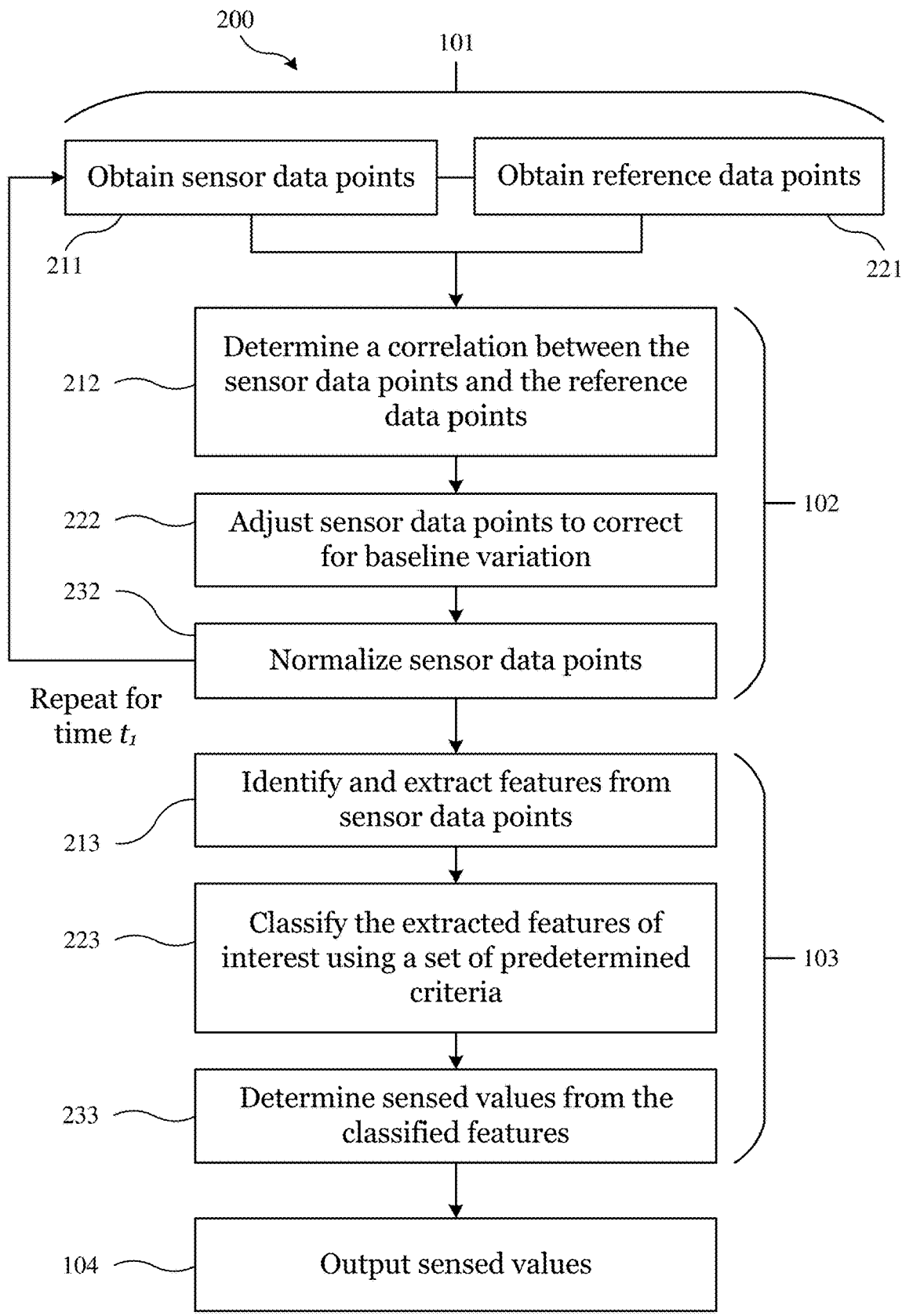
FIG. 2 illustrates another method of sensing in which baseline variation is corrected based on correlation with reference data points in accordance with an embodiment of the invention.

FIG. 2 illustrates another method of sensing in which baseline variation is corrected based on correlation with reference data points in accordance with an embodiment of the invention.

Referring to FIG. 2, a method 200 of sensing includes the following steps. Step 211 includes obtaining sensor data points and step 221 includes obtaining reference data points. Steps 211 and 221 may be executed at the same time or at different times. In various embodiments, steps 211 and 221 are part of a step 101 of obtaining sensing data such as previously described in reference to FIGS. 1A and 1B. Sensor data points may be obtained by recording measurements from sensors configured to respond to sensing events. Reference data points may be obtained by recording measurements from reference sensors that are configured to be used as a reference or that have an identifiable trait that may be used as a reference. Only as an illustration, a gas sensing system may comprise one reference sensor for providing the reference data and a plurality of sensors for measuring different type of target analytes so as to generate sensor data. For example, the sensor data may comprise detected concentration for each target analyte that is being measured.

Step 212 includes determining a correlation between the sensor data points and the reference data points. The correlation may be determined by comparing the sensor data points and reference data points. The existence of a correlation between the sensor data points and the reference data points may indicate the existence of an external influence that is unrelated to target analyte of the sensor. For example, the sensor data points may be obtained from a sensor that is sensitive to the presence of a target analyte while the reference data points may be obtained from a reference sensor that is not affected by the presence of the target analyte. A correlation between the sensor data points and the reference data points may then indicate that influences unrelated to the target analyte affect the sensor and the reference sensor in a similar manner.

In some embodiments, the reference data points may be measurements from an environmental sensor. The output of the environmental sensor may be chosen to be unrelated to the sensing target. For example, the environmental sensor may measure an environmental factor (e.g., temperature, humidity, pressure, and others) that is known to affect the performance of the sensing sensor. Accordingly, the environmental sensor may be a temperature sensor, a humidity sensor, or a pressure sensor, for example. In this way a correlation between the environmental factor and the sensor response of the sensing sensor can be determined by using the correlation between the sensor data points and the reference data points.

In other embodiments, the reference data points may be measurements from a structural reference sensor that has a similar structure as a sensing sensor, but is unresponsive to the sensing target. Since the output of the structural reference sensor is not affected by the sensing target, a correlation between the sensor output and the structural reference sensor output may be related to an external influence, which contributes to baseline variation. In some embodiments, the reference data points may be obtained from a combination of environmental sensor and structural reference sensor measurements.

Step 222 includes adjusting the sensor data points to correct for baseline variation. After the adjustment, the sensor data points may reflect a sensor output with a constant baseline. For example, an equation relating the correlation and the reference points to baseline values may be used to obtain a correction for each sensor data point. Possible equations include linear regression, multiple regression, $n^{th}$ order polynomial fitting such as quadratic, cubic, quartic, etc., logarithmic fitting, and exponential fitting, as examples. As an illustration, the baseline used as a reference by the sensor data points is made constant using the reference data points. That is, background noise and/or baseline variation in the signal caused by external effects may be significantly reduced or removed from the sensor data points.

Step 232 includes normalizing the sensor data points. In some cases, the measured sensor response resulting in the set of sensor data points may need to be dimensionless to facilitate accurate post processing. For example, the sensor data points may be represented as a percentage or a ratio rather than in specific units of measure.

In various embodiments, step 232 is optional and may be omitted depending on specific post processing implementations. In some embodiments, steps 212, 222, and 232 are part of a step 102 of preprocessing the sensing data such as previously described in reference to FIGS. 1A and 1B.

Steps 211, 221, 212, 222, and 232 may be repeated for a first period of time t1. For example, it may be advantageous in some implementations to gather a large amount of data before each post processing step in order to obtain accurate sensing events and sensed values. In this case, obtaining and preprocessing sensing data may be performed for a predetermined amount of time to accumulate a sufficient quantity of data points, and then the preprocessed data set can be sent for post processing. In some cases, first period of time $t_1$ may be referred to as a sampling time.

Still referring to FIG. 2, step 213 includes identifying and extracting features from the sensor data points. For example, a feature may be identified by determining that a value exceeds a predetermined threshold. Alternatively, the beginning and end of a feature may be identified by determining that a rate of change of the sensing data crosses a predetermined threshold. In addition to features, so-called regions of interest may also be identified. In some cases feature may be considered synonymous with region of interest, but this may depend on specific sensing implementations. The identification of regions of interest and/or features may include complex analysis of the shape of a curve defined by the sensing data. Following identification, the regions of interest and/or features may be extracted by removing remaining data points.

Step 223 includes classifying the extracted features using a set of predetermined criteria. Classification of the extracted features may be used to determine the most important features and/or remove features that do not contain sensing information. For example, removal of features may be performed in a dimensional reduction step. A set of features may be reduced to the most important features using dimensional analysis methods such as principal component analysis (PCA), Kernel PCA, linear discriminant analysis (LDA), Random forests, etc. Classification of the extracted features may be performed using a standard machine learning algorithm such as Naïve Bayes, logistic regression, decision trees, support vector machines, neural networks, K-nearest neighbors, etc. Once classified, the data can be cross referenced with stored calibration values (such as a look-up table) to extract sensed values.

After classifying the extracted features, step 233 includes determining sensed values from the classified features. In various embodiments, steps 213, 223, and 233 are part of a step 103 of post processing the sensing data such as previously described in reference to FIGS. 1A and 1B. Step 104 includes outputting sensed values and is as previously described.

Figure 3:
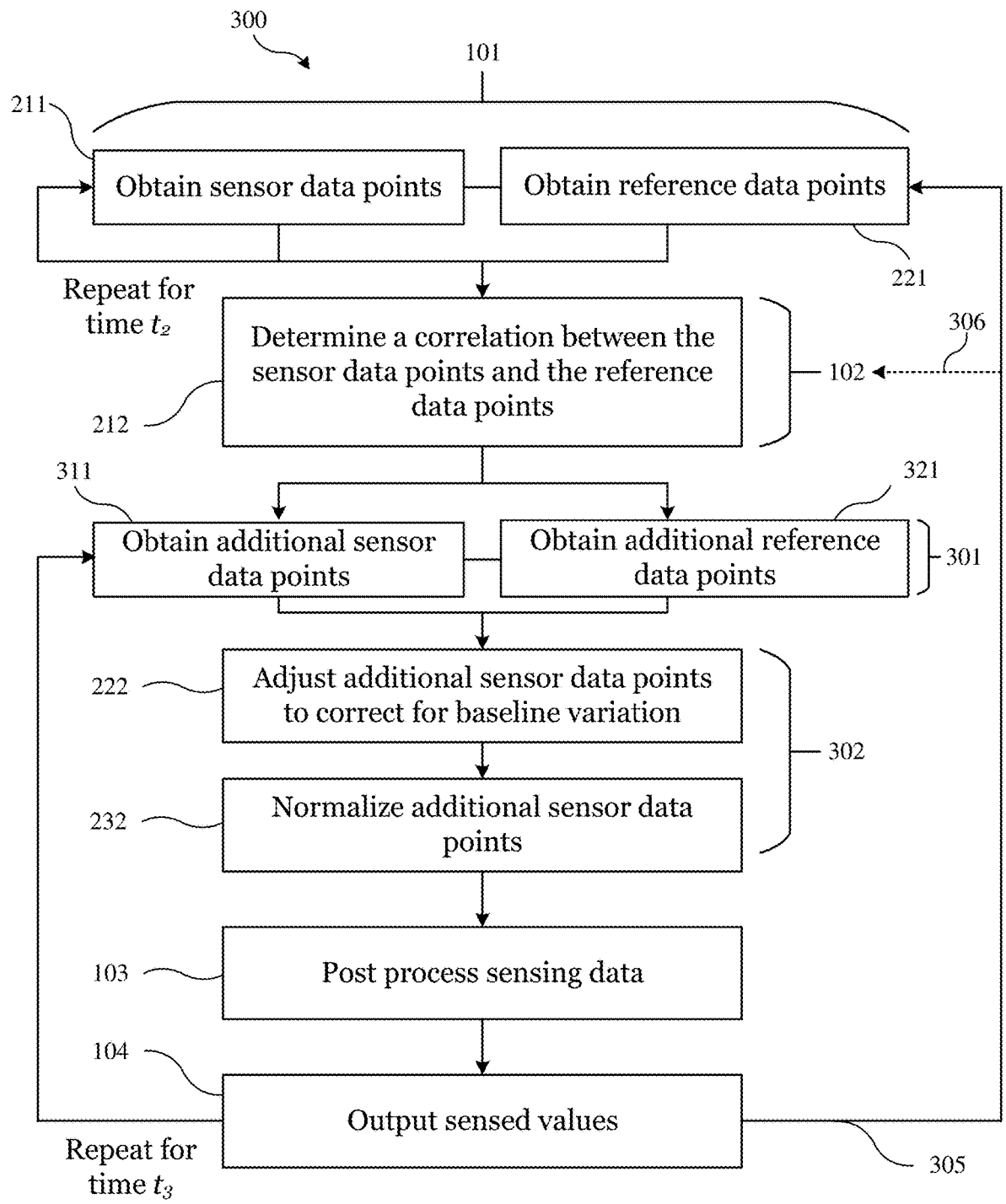
FIG. 3 illustrates still another method of sensing in which baseline variation is corrected based on correlation with reference data points in accordance with an embodiment of the invention.

FIG. 3 illustrates still another method of sensing in which baseline variation is corrected based on correlation with reference data points in accordance with an embodiment of the invention.

Referring to FIG. 3, the method 300 of sensing includes the following steps. Step 211 includes obtaining sensor data points and step 221 includes obtaining reference data points and may be as previously described with respect to FIG. 2. Additionally, steps 211 and 221 may be part of a step 101 of obtaining sensing data that may be repeated for a second period of time $t_2$ before the sensing data is processed in subsequent steps. In some applications, the second period of time $t_2$ may be referred to as a sampling time.

Step 212 includes determining a correlation between the sensor data points and the reference data points and may be part of a step 102 of preprocessing the sensing data that has been obtained in step 101. Method 300 differs from method 200 in that the step 212 of determining the correlation is performed after the second period of time $t_2$ has passed rather than multiple times over a first period of time $t_1$ as in method 200.

After sensing data has been obtained in step 101 and a correlation has been determined in step 212, an additional set of sensing data may be obtained in a step 301 of obtaining additional sensing data. Step 301 includes a step 311 of obtaining additional sensor data points and a step 321 of obtaining additional reference data points similar to steps 211 and 221 as previously described.

The correlation determined in step 212 may then be used in conjunction with the additional sensing data for adjusting the additional sensor data points to correct for baseline variation in step 222. An optional step 232 includes normalizing the additional sensor data points. Steps 222 and 232 of method 300 are similar to corresponding steps in method 200 and may be part of a step 302 of preprocessing additional sensing data.

Following preprocessing of the additional sensing data, a step 103 of post processing data and a step 104 of outputting sensed values is performed. Steps 103 and 104 may be as previously described. Steps 301, 302, 103 and 104 may be repeated for a third period of time $t_3$ during which the same correlation that is determined in step 212 may be used to correct any number of additional sensing data sets. Additionally, step 301 may be repeated for a sampling time similar to step 101.

Any of the described steps may also be performed serially or in parallel. For example, a sensing system may acquire new data in steps 101 or 301 at the same time as previously acquired data is being processed in steps 102, 302, and/or 103. Similarly, output values may be display in step 104 while new sensing data sets are being obtained and processed.

In contrast to method 200, in method 300 a first sensing data set is used to determine the correlation and subsequent sensing data sets are corrected using the correlation and the optionally normalized. For example, in one scenario, no sensing events may take place during the second period of time $t_2$. This may advantageously improve the accuracy of the correlation that is determined between the sensor data points and the reference data points. During the third period of time $t_3$ sensing events may or may not occur, and the sensing system may output sensed values that are adjusted to correct for baseline variation using the correlation determined from sensing data with no detection events.

After a predetermined amount of time or in response to a determination that a new correlation should be determined, a step 305 of beginning the process anew at step 101 may be performed. In some embodiments, step 305 may be performed after determining that the sensed values that are output in step 104 have been below a threshold for a predetermined amount of time. In other embodiments, step 305 may be performed when the number of sensing events identified in step 103 is below a predetermined threshold.

As an example, second time $t_2$ may be 10 seconds, third period of time $t_3$ may be 30 seconds, and step 305 may be performed after each expiration of the third period of time $t_3$. In this case a correlation is determined every 40 seconds after 10 seconds of obtaining sensing data. The correlation is then used to correct for baseline variation on additional sensing data that is continuously gathered for 30 seconds. In this example, sensed values are output for 75% of every cycle. During the 25% downtime, sensor system may be refreshed to improve the sensing accuracy during the 75% uptime. Any combination of values of the second and third period of time $t_2$ and $t_3$ is possible and may be chosen based on a potential tradeoff between accuracy of the correction to the baseline variation and the desired uptime of the sensor. In some embodiments, the values of the second and third periods of time $t_2$ and $t_3$ may be dynamic or manually adjustable.

As another example, the third period of time $t_3$ may extend until a predetermined amount of time without a sensing event has passed. Step 305 and optional step 306 may then be performed. The sensing data points and reference data points obtained during the time without a sensing event may be used in step 212 to determine a new correlation. In this example, sensor downtime may be advantageously reduced by only determining coefficients when no sensor events are occurring.

Optionally, step 101 may be omitted when performing step 305 which is shown as a dotted arrow 306 proceeding directly to step 102. For example, the criteria to perform step 305 may coincide with the criteria to use a set of sensing data in step 212 enabling step 101 to be omitted in some or all iterations of method 300.

Figure 4:
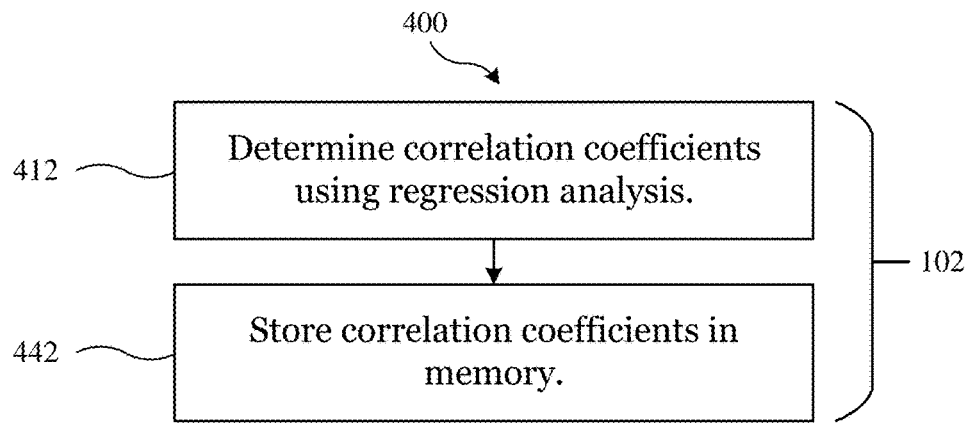
FIG. 4 illustrates a method of preprocessing sensing data in accordance with an embodiment of the invention.

FIG. 4 illustrates a method of preprocessing sensing data in accordance with an embodiment of the invention.

Referring to FIG. 4, a method 400 of preprocessing sensing data includes a step 412 of determining correlation coefficients using regression analysis. The regression analysis may be any suitable method in which a relationship between a dependent variable and one or more in independent variables. Possible regression analysis methods may include linear regression, ordinary least squares regression, polynomial regression, nonlinear regression, and the like. In one embodiment, the regression analysis used in step 412 is simple linear regression.

An example of using simple linear regression in step 412 to determine correlation coefficients is as follows. A sensing system may include a sensor with resistance $R_S$ that is sensitive to fluctuations in temperature. The sensing system may include a heating element with a resistance $R_H$ that is variable in time t. The temperature of the heating element may depend on the heating element resistance $R_H$. In a previous step of obtaining sensing data, a set of sensor data points $R_S$ and a set of reference data points $R_H$ may be obtained over a period of time $t_0 \le t \le t_f$. Correlation coefficients $C_0$ and $C_1$ may then be determined from the first order polynomial equation below.

$$R_S(t)=C_1 R_H(t)+C_0$$

As another example of using simple linear regression in step 412, a sensing system may include a sensor with resistance $R_S$ that is sensitive to fluctuations in temperature. The sensing system may also include a heating element driven by a current that is regulated using a closed loop control such as pulse-width modulation (PWM) modes or proportional-integral-derivative (PID) control. The sensing system may also include a temperature sensor located near the sensor that measures the ambient temperature T. Since the current through the heating element is regulated, the baseline variation of the sensor may be primarily caused by fluctuations in ambient temperature. In a previous step of obtaining sensing data, a set of sensor data points $R_S$ and a set of reference data points T may be obtained over a period of time $t_0 \le t \le t_f$. Correlation coefficients $C_0$ and $C_1$ may then be determined from the first order polynomial equation below.

$$R_S(t)=C_1 T(t)+C_0$$

As still another example, multiple linear regression may be used in step 412 as follows. A sensing system may include a sensor with resistance $R_S$ that is sensitive to fluctuations in temperature and humidity. The sensing system may also include a heating element, a humidity sensor, and an array of temperature sensors located near both the heating element and the sensor. The array of temperature sensors may measure the temperature T at the sensor and the humidity sensor may measure the humidity RH at the sensor. In a previous step of obtaining sensing data, a set of sensor data points $R_S$ and two sets of reference data points T, RH may be obtained over a period of time $t_0 \le t \le t_f$. Correlation coefficients $C_0$, $C_1$, and $C_2$ may then be determined from the equation below.

$$R_S(t)=C_2 RH(t)+C_1 T(t)+C_0$$

In other embodiments, such as when there is a nonlinear dependence on the reference data points, the regression analysis used in step 412 is polynomial regression. In still other embodiments, such as for very complex sensing systems where complete understanding may be difficult, regression analysis may be replaced with machine learning algorithms.

In various embodiments, step 412 may be performed for each sensor in an array of sensors resulting in a set of correlation coefficients for each sensor. Alternatively, step 412 may be performed using the average output of a sensor array or for the average output of subsets of a sensor array.

Following the determination of correlation coefficients in step 412, the correlation coefficients may be stored in a computer-readable memory for future use in an optional step 442. Alternatively, the correlation coefficients may be determined immediately prior to every use and not stored in a memory. The correlation coefficients that are stored in step 442 may overwrite previously stored correlation coefficients and/or may be appended to a history of stored correlation coefficients. The history of correlation coefficients may be used to ensure that the new correlation coefficients are reasonable and for potential troubleshooting of the sensor. The steps 412 and 442 may be part of a step 102 of preprocessing the sensing data as previously described.

Figure 5:
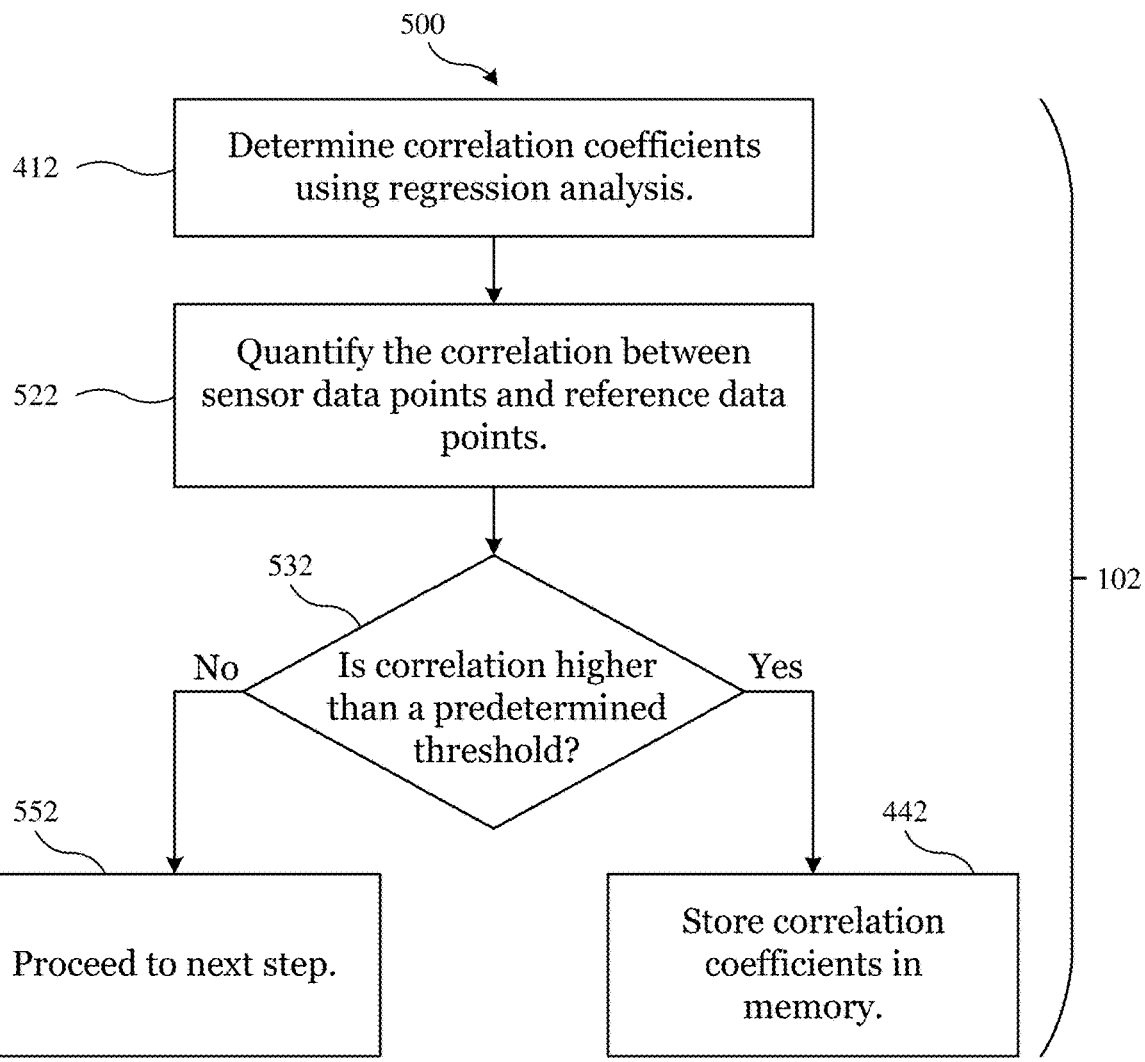
FIG. 5 illustrates another method of preprocessing sensing data in accordance with an embodiment of the invention.

FIG. 5 illustrates another method of preprocessing sensing data in accordance with an embodiment of the invention.

Referring to FIG. 5, a method 500 of preprocessing sensing data includes a step 412 of determining correlation coefficients using regression analysis and a step 442 which may be a previously described with respect to FIG. 4. In contrast to method 400, method 500 includes a step 522 of quantifying the correlation between the sensor data points and the reference data points after step 412. In various embodiments, the quantity determined in step 522 may be a coefficient of determination $R^2$. The coefficient of determination $R^2$ may be used as an indicator of the level of correlation between the sensor data points and the reference data points. Other indicators such as the square of the Pearson correlation coefficient may also be used and may be apparent to those of ordinary skill in the art.

Step 532 includes a branching step that determines if the quantity determined in step 522 is higher than a predetermined threshold. For example, a sensing system may exhibit desired performance using the correlation coefficients determined in step 412 when the coefficient of determination $R^2$ is above 0.91. In this example, the predetermined threshold for step 522 may be 0.91. When the coefficient of determination $R^2$ is greater than 0.91, the correlation coefficients are stored in memory in step 442. If the coefficient of determination $R^2$ is less than or equal to 0.91, a step 552 is performed which does not store the new correlation coefficients in memory and which continues on to a later step. In this way, an older set of correlation coefficients which meet the required correlation may be used instead of new set that is not sufficiently correlated.

As shown in FIG. 5, the steps 412, 522, 532, 552, and 442 may be part of a step 102 of preprocessing the sensing data as previously described.

Figure 6:
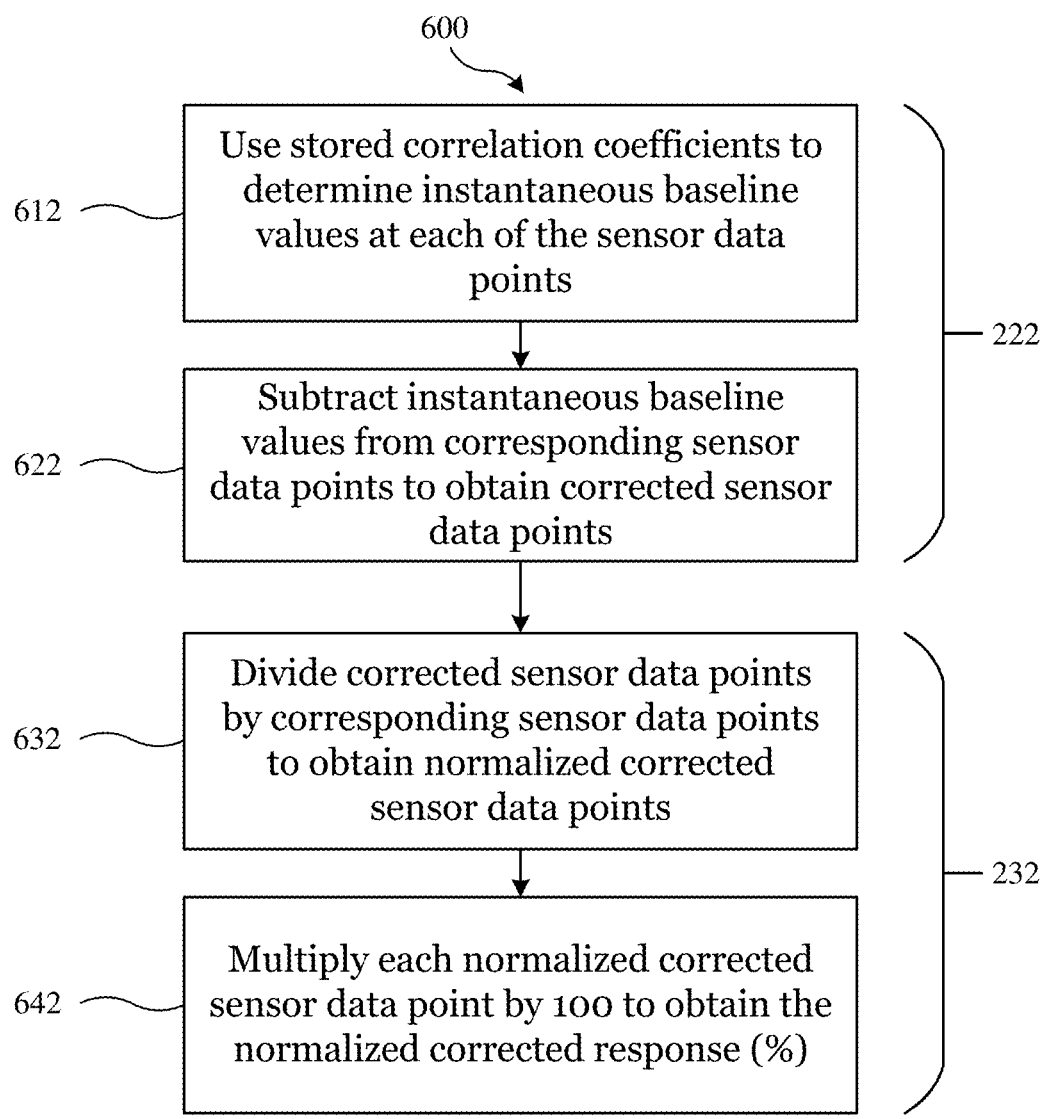
FIG. 6 illustrates a method of adjusting a baseline to correct baseline variation and normalizing sensor data points in accordance with an embodiment of the invention.

FIG. 6 illustrates a method of adjusting a baseline to correct baseline variation and normalizing sensor data points in accordance with an embodiment of the invention. The method illustrated in FIG. 6 may be incorporated as appropriate into the methods of any of the previously described embodiments.

Referring to FIG. 6, a method 600 of adjusting a baseline to correct baseline variation and normalizing sensor data points includes a step 612 of using stored correlation coefficients to determine instantaneous baseline values at each of the sensor data points. For example, in the first scenario given in reference to FIG. 4, an equation is used to determine a set of correlation coefficients $C_0$ and $C_1$. The same equation may be used to determine the instantaneous baseline values $R_{S,baseline}(t)$ for each time t using the stored correlation coefficients $C_0$ and $C_1$ and a new reference data point $R_{H,new}(t)$ corresponding to each new sensor data point $R_{S,new}(t)$ as shown below.

$$R_{S,baseline}(t) = C_1 R_{H,new}(t) + C_0$$

In other words, any equation that is used in determining a set correlation coefficients such as in step 412 may be used in conjunction with the set of correlation coefficients and new reference data points to determine a set of instantaneous baseline values in step 612.

Following step 612, the step 622 includes subtracting instantaneous baseline values $R_{S,baseline}(t)$ from corresponding new sensor data points $R_{S,new}(t)$ to obtain corrected sensor data points $R_{S,corrected}(t)$. Continuing with the previous example, an equation describing step 622 might be as given below.

$$R_{S,corrected}(t) = R_{S,new}(t) - R_{S,baseline}(t) = R_{S,new}(t) - [C_1 R_{H,new}(t) + C_0]$$

At this point corrected sensor data points $R_{S,corrected}(t)$ have been determined using correlation coefficients. Steps 612 and 622 may be part of a step 222 of adjusting sensor data points to correct for baseline variation which may be as previously described.

Following the correction for baseline variation, the corrected sensor data points may optionally be normalized in step 632 and represented as a relative percentage in step 642. Steps 632 and 642 may be part of a step 232 of normalizing sensor data points which may be as previously described.

Step 632 includes dividing the corrected sensor data points $R_{S,corrected}(t)$ by corresponding new sensor data points $R_{S,new}(t)$ and results in normalized corrected sensor data points. Additionally, step 642 includes multiplying each normalized corrected sensor data point by 100 to obtain a set of normalized corrected sensor data points represented as a relative percentage $R_{S,normalized}(t)$. The set of normalized corrected sensor data points may be referred to as a normalized corrected response. An equation using the scenario of the above example is given below.

$$R_{S,normalized}(t) = 100 \cdot \frac{R_{S,corrected}(t)}{R_{S,new}(t)} = 100 \cdot \frac{R_{S,new}(t) - [C_1 R_{H,new}(t) + C_0]}{R_{S,new}(t)}$$

In other embodiments step 642 may be omitted and the normalized corrected sensor data points may be represented as a relative ratio. In still other embodiments, steps 632 and 642 may be omitted and the corrected sensor data points may be post processed.

It should be noted that in the method embodiments described herein, like reference numbers between embodiments may represent interchangeability and/or like features. For example, method 600 as described in reference to FIG. 6 includes steps 222 and 232 which are also described in reference to FIGS. 2 and 3. Therefore, steps 222 and 232 as described in method 600 may be incorporated into methods 200 and 300 and so on.

FIGS. 7-18 illustrate various sensor devices which may be included in implementations of sensing systems that are configured to perform the methods described in reference to FIGS. 1-6. All similarly numbered elements in FIGS. 7-18 refer to like elements between the various embodiments.

Figure 7:
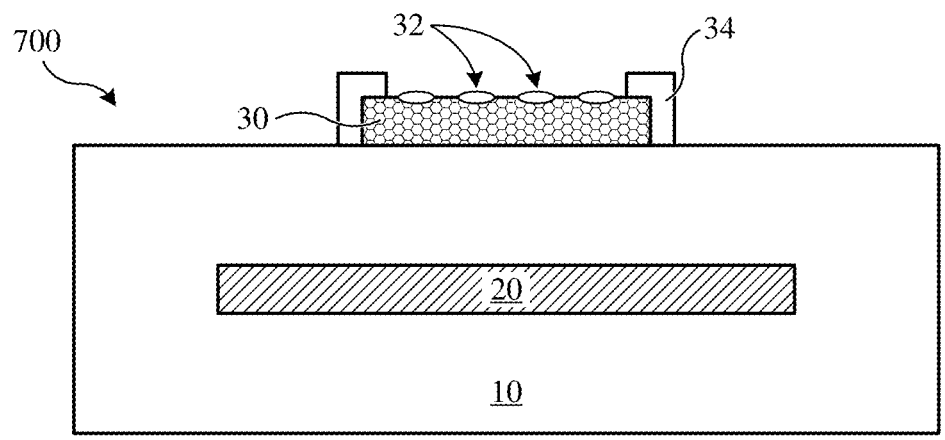
FIG. 7 illustrates an example sensor device including a substrate, a heating element, and a sensor in accordance with an embodiment of the invention.

FIG. 7 illustrates an example sensor device including a substrate, a heating element, and a sensor in accordance with an embodiment of the invention.

Referring to FIG. 7, a sensor device 700 includes a sensor 30 disposed on a substrate 10. The sensor 30 may be any suitable type of sensor such as a chemical sensor configured to detect a target analyte or group of target analytes. In various embodiments, the sensor 30 is a gas sensor. In some embodiments, the gas sensor is a resistive gas sensor, and in one embodiment, sensor 30 is a graphene-based resistive gas sensor. The graphene-based resistive gas sensor may generate sensing events by monitoring the change in resistance of one or more sheets of graphene, which is modulated by gas molecules being adsorbed and desorbed from the surface of the graphene. The sensor resistance may decrease when adsorbed gas species provide donor electrons to the graphene surface. Alternatively, the resistance may decrease when adsorbed gas species draw electrons away from the path of conduction.

The transduction method for the graphene-based gas sensor may also be different in various embodiments. For example, rather than a resistive gas sensor, sensor 30 may be a capacitive gas sensor and is a graphene-based capacitive gas sensor in one embodiment. Other possible transduction methods include work function monitoring, inversion n-type to p-type and may be apparent to those of ordinary skill in the art.

Sensor 30 may be configured to have selectivity towards a target analyte. For example, sensor 30 may selectively sense concentrations of volatile organic compounds (VOCs) in the ambient atmosphere. In various embodiments, sensor 30 may be configured to sense volatile gases such as hydrocarbons, methylene chloride, formaldehyde, and the like.

The sensor 30 may be sensitive to one or more environmental factors that affect the baseline of the sensor 30. For example, environmental factors may include fluctuations in temperature, humidity, pressure, electric field, magnetic field, composition of the ambient atmosphere, concentration of species in the ambient atmosphere, and the like. In the specific example of a graphene-based resistive gas sensor, fluctuations in temperature may affect the performance of the sensor 30.

The sensor 30 may be suspended between two or more electrodes 34. The electrodes 34 may include a conductive material and may be a patterned metal in various embodiments. For example, the electrodes 34 may include copper (Cu), silver (Ag), gold (Au), aluminum (Al), tungsten (W), and the like.

In some embodiments, the sensor 30 may also include surface modifications 32. The surface modifications 32 may be chemical groups attached to the surface of sensor 30 to increase the sensitivity of sensor 30 to target analytes and/or reduce the sensitivity of sensor 30 to environmental factors or species other than target analytes. In other embodiments, the surface modifications 32 may be a protective coating and may cover all or most of the sensor 30.

The substrate 10 may be any suitable substrate. In various embodiments, substrate 10 is a laminate substrate and is a printed circuit board in one embodiment. In other embodiments, substrate 10 is a semiconductor substrate and is part of a monolithic integrated circuit chip including sensor 30. In one embodiment, substrate 10 is a silicon substrate and sensor 30 is included in an integrated circuit. In another embodiment, substrate 10 is a ceramic substrate. Substrate 10 may also be a metallic substrate or include a metallic substrate. In some embodiments, substrate 10 may be packaged to form a sensor package including sensor 30.

A heating element 20 may be included on or within substrate 20. The heating element 20 may heat the sensor 30 and sensor device 700 in order to maintain an optimal operating temperature or range of operating temperatures. For example, the heating element 20 may heat the sensor 30 to 200° C. in one embodiment. In another embodiment, the heating element 20 may heat the sensor 30 to 400° C. In the specific case of a resistive gas sensor, the temperature may need to be elevated to facilitate desorption of gas molecules for continued sensing. In some cases, refresh cycles may be used to heat the sensor 30 to a temperature well above the normal operating temperature in order to remove all species from the surface of sensor 30 before beginning a new data acquisition period.

The heating element 20 may also be used as a reference for baseline variation of sensor 30. For example, the resistance of heating element 20 may be recorded periodically during data acquisition periods and used as reference data points when correcting for baseline variation of sensor 30.

The heating element 20 may be a metal conductor in one embodiment. In other embodiments, the heating element 20 may be a microelectromechanical systems (MEMS) heater integrated into a semiconductor substrate. The heating element 20 and/or sensor 30 may also be suspended over an opening in substrate 10. This may facilitate increased interaction with the ambient atmosphere as well as reduce heat loss in the heating element 20.

Figure 8:
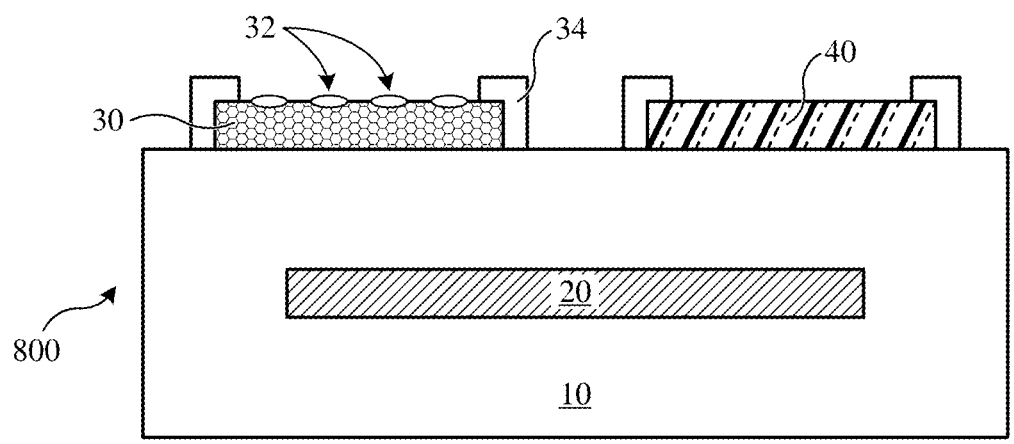
FIG. 8 illustrates an example sensor device including a substrate, a heating element, a sensor, and an environmental sensor in accordance with an embodiment of the invention.

FIG. 8 illustrates an example sensor device including a substrate, a heating element, a sensor, and an environmental sensor in accordance with an embodiment of the invention.

Referring to FIG. 8, a sensor device 800 includes a sensor 30 and a heating element 20 attached to a substrate 10 as previously described. In contrast to sensor device 700, sensor device 800 also includes an environmental sensor 40. The environmental sensor 40 may be a temperature sensor, humidity sensor, pressure sensor, and the like. The environmental sensor 40 may be configured to measure reference data points to for use in correcting the baseline variation of sensor 30 as described in previous methods.

Figure 9:
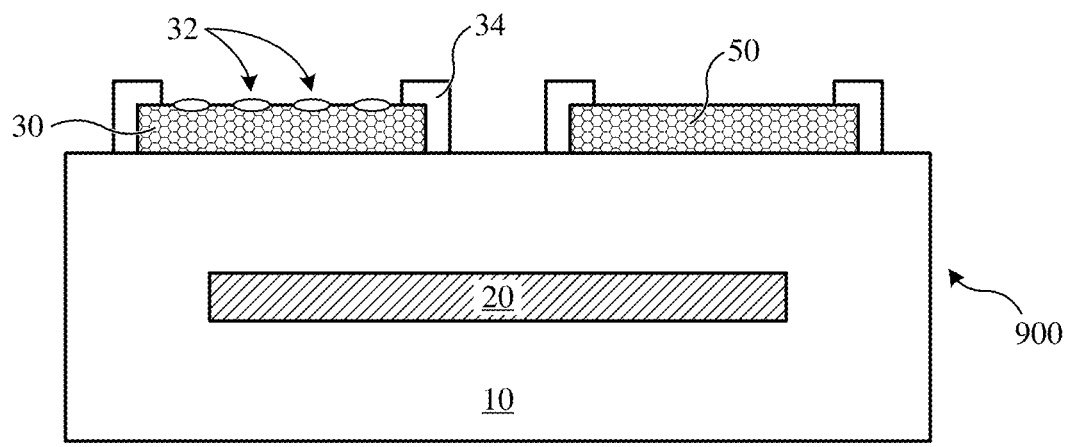
FIG. 9 illustrates an example sensor device including a substrate, a heating element, a sensor, and a reference sensor in accordance with an embodiment of the invention.

FIG. 9 illustrates an example sensor device including a substrate, a heating element, a sensor, and a structural reference sensor in accordance with an embodiment of the invention.

Referring to FIG. 9, a sensor device 900 includes a sensor 30 and a heating element 20 attached to a substrate 10 as previously described. Instead of the environmental sensor 40 included in sensor device 800, sensor device 900 includes a structural reference sensor 50. The structural reference sensor 50 may be sufficiently similar in structure or function to sensor 30 so as to provide reference data points for use in correcting the baseline variation of sensor 30.

For example, sensor 30 and structural reference sensor 50 may both be graphene-based resistive gas sensors, but structural reference sensor 50 may not include surface modifications 32. Alternatively, the surface of sensor 30 is bare graphene and the surface of structural reference sensor 50 is coated or otherwise modified to be unresponsive to the target analyte of sensor 30. In this way, the contribution of the sensing target may be removed from the signal of the structural reference sensor 50 and only the effects of environmental factors remain. Significant correlation between the sensor 30 and the structural reference sensor 50 may then be primarily caused by environmental factors and reflect baseline variation in both sensors.

Figure 10:
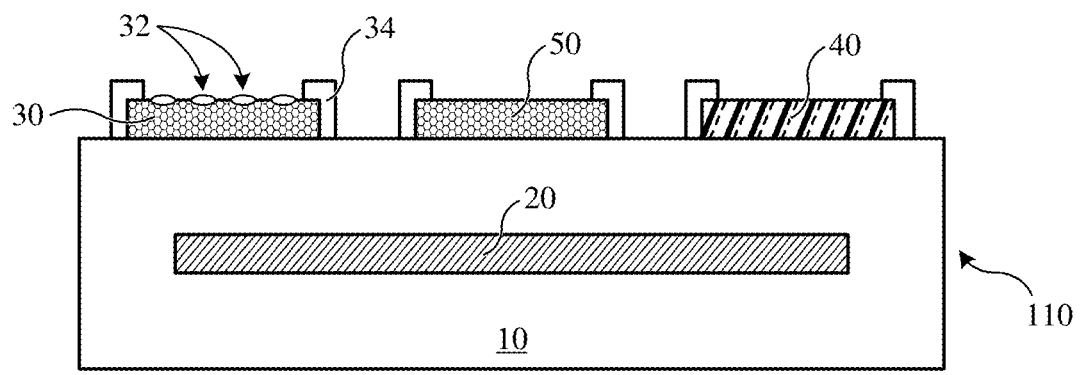
FIG. 10 illustrates an example sensor device including a substrate, a heating element, a sensor, an environmental sensor, and a reference sensor where the environmental sensor is located on the substrate in accordance with an embodiment of the invention.

FIG. 10 illustrates an example sensor device including a substrate, a heating element, a sensor, an environmental sensor, and a reference sensor where the environmental sensor is located on the substrate in accordance with an embodiment of the invention.

Referring to FIG. 10, a sensor device 110 includes a sensor 30, an environmental sensor 40, a reference sensor 50, and a heating element 20 attached to a substrate 10. Any combination of the heating element 20, environmental sensor 40, and structural reference sensor 50 may be used to obtain reference data points to correct for baseline variation of sensor 30.

Figure 11:
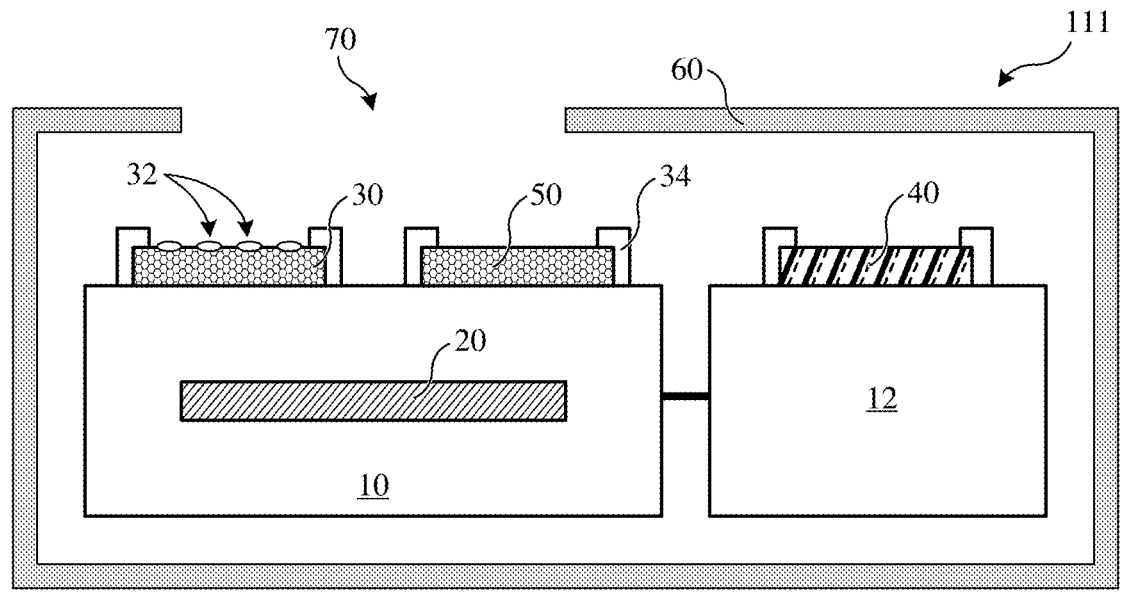
FIG. 11 illustrates another example sensor device including a substrate, a heating element, a sensor, an environmental sensor, and a reference sensor where the environmental sensor is located on a second substrate in accordance with an embodiment of the invention.

FIG. 11 illustrates another example sensor device including a substrate, a heating element, a sensor, an environmental sensor, and a structural reference sensor where the environmental sensor is located on a second substrate in accordance with an embodiment of the invention.

Referring to FIG. 11, a sensor device 11 includes a sensor 30, a structural reference sensor 50, and a heating element attached to a substrate 10 as previously described. However sensor device 11 differs from sensor device 110 in that an included environmental sensor 40 is attached to a second substrate 12 rather than substrate 10. The substrate 10 is operatively coupled to the second substrate 12 and both are contained in a package 60.

The second substrate 12 may include a processor such as an application-specific integrated circuit (ASIC) or a field-programmable gate array (FPGA). The processor may be configured to perform any of the method steps as described in previous embodiments such as obtaining sensing data, preprocessing the sensing data, post processing the sensing data, and outputting sensed values. The substrate 10 and the second substrate 12 may be rigidly attached to the package 60. However, in some embodiments, the substrate 10 and the second substrate 12 may be elastically attached to the package 60.

The package 60 includes an opening 70 which facilitates interactions of sensor 30, environmental sensor 40, and reference sensor 50 with the ambient environment. It should be noted that although package 60 and opening 70 are only illustrated in FIG. 11, package 60 and opening 70 may be included in all embodiment sensor device described herein and apparent to those of ordinary skill in the art.

Figure 12:
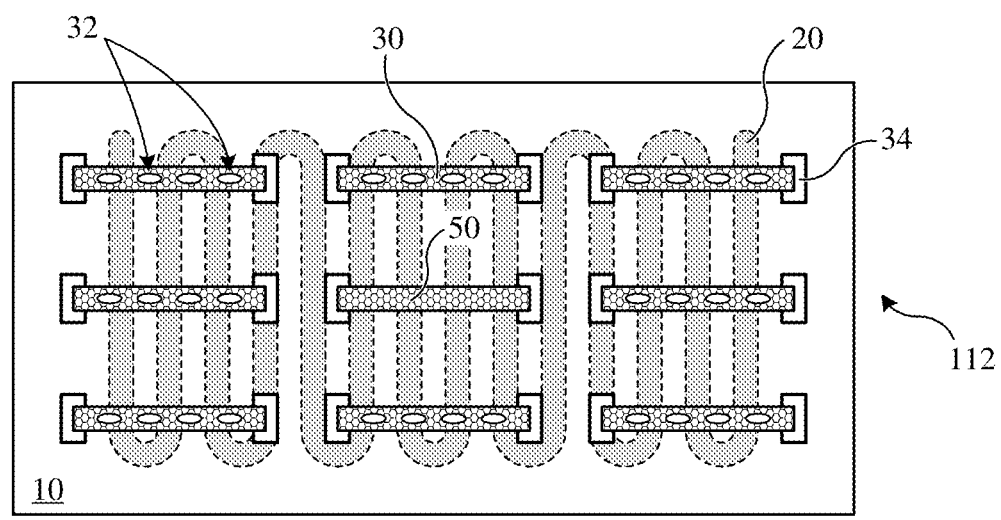
FIG. 12 illustrates a top view of an example sensor device including multiple sensors and a reference sensor in accordance with an embodiment of the invention.

FIG. 12 illustrates a top view of an example sensor device including multiple sensors and a reference sensor in accordance with an embodiment of the invention.

Referring to FIG. 12, a sensor device 112 includes multiple sensors 30 and a centrally located structural reference sensor 50 attached to a substrate 10. A heating element 20 is also included on or within substrate 10 which provides heat to the sensors 30 and structural reference sensor 50. In this embodiment, eight sensors 30 form and array of sensors 30 and a single structural reference sensor 50 is included in the center of a box arrangement of sensors 30.

However, any arrangement of multiple sensors 30 and a structural reference sensor 50 is possible. For example, a 5×5 array of sensors 30 may be located on the left side of substrate 10 while a structural reference sensor 50 is located on the right side. The number and arrangement of sensors 30 and structural reference sensor 50 may depend on specific application and is not limited to exactly the patterns illustrated in this or other embodiments.

Figure 13:
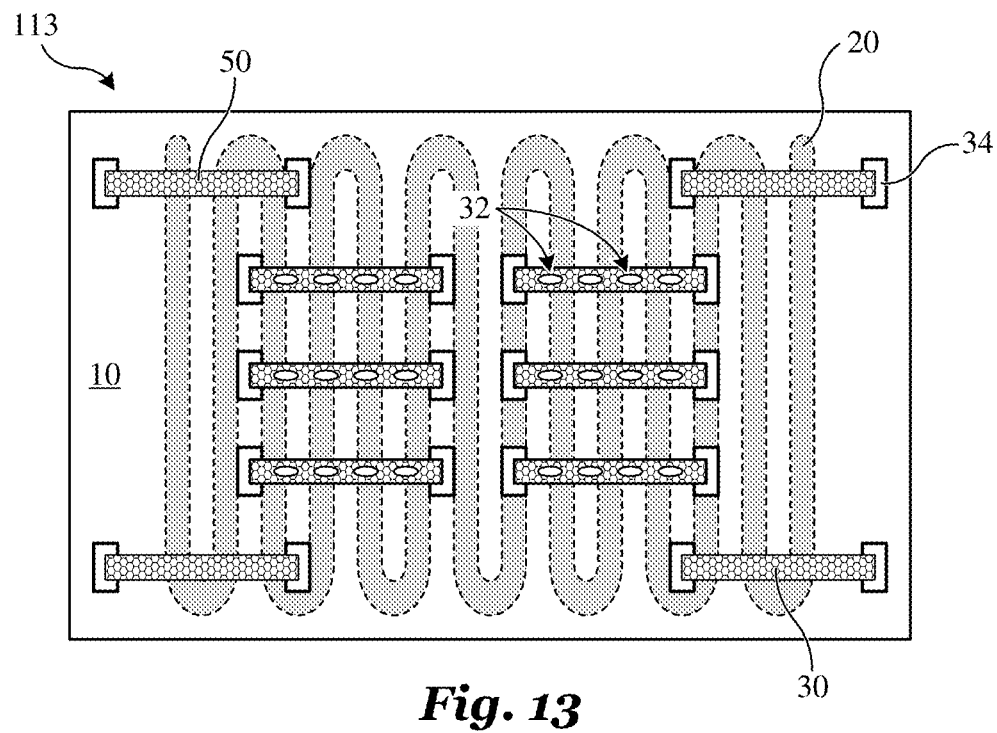
FIG. 13 illustrates a top view of an example sensor device including multiple sensors and multiple reference sensors in accordance with an embodiment of the invention.

FIG. 13 illustrates a top view of an example sensor device including multiple sensors and multiple reference sensors in accordance with an embodiment of the invention.

Referring to FIG. 13, a sensor device 113 includes multiple sensors 30 arranged in an array in a central region of a substrate 10 and four structural reference sensors 50 located in respective corner regions of the substrate 10. The four structural reference sensors 50 may be averaged for use in determining correlation coefficients or a multiple regression may be used with four dependent variables as previously described. In all embodiments, the heating element may also be used as a reference.

Figure 14:
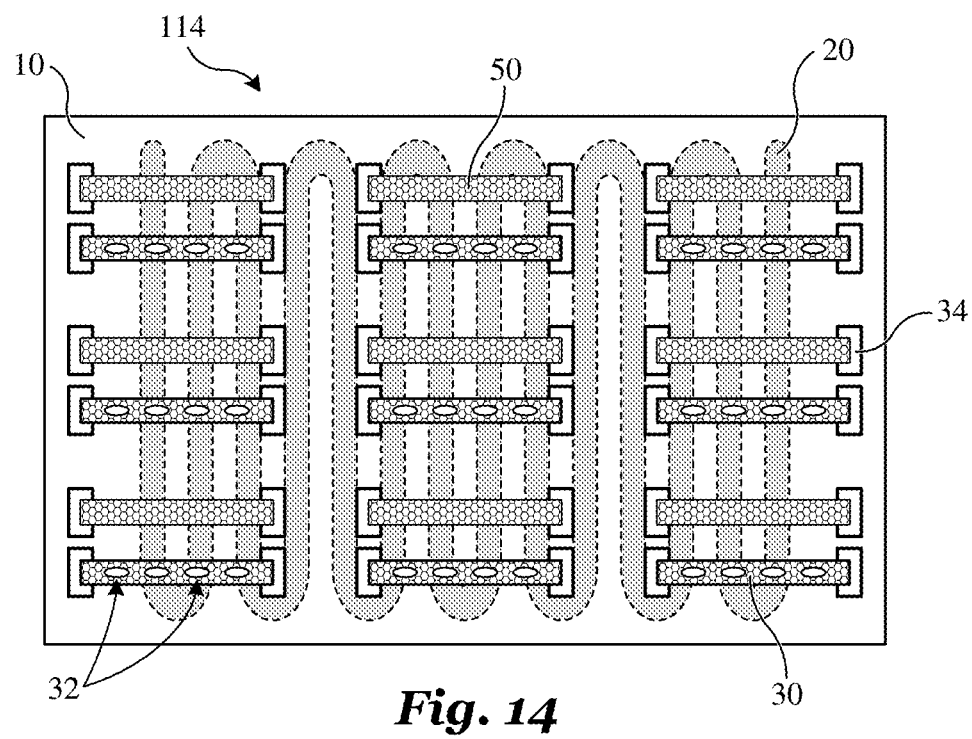
FIG. 14 illustrates a top view of an example sensor device including multiple pairs of a sensor and a reference sensor in accordance with an embodiment of the invention.

FIG. 14 illustrates a top view of an example sensor device including multiple pairs of a sensor and a reference sensor in accordance with an embodiment of the invention.

Referring to FIG. 14, a sensor device 114 includes multiple pairs of a sensor 30 and a structural reference sensor 50 arranged in an array on a substrate 10. The substrate 10 also includes a heating element 20 as previously described. In this arrangement a structural reference sensor 50 may be used to correct the baseline variation for each corresponding sensor 30. This may be useful if there is variation between sensors 30 over the substrate 10 or if there are multiple types of sensor 30 on the same substrate 10. Additionally, the corrected sensor data from each sensor 30 may be treated individually or averaged before post processing depending on specific application.

Figure 15:
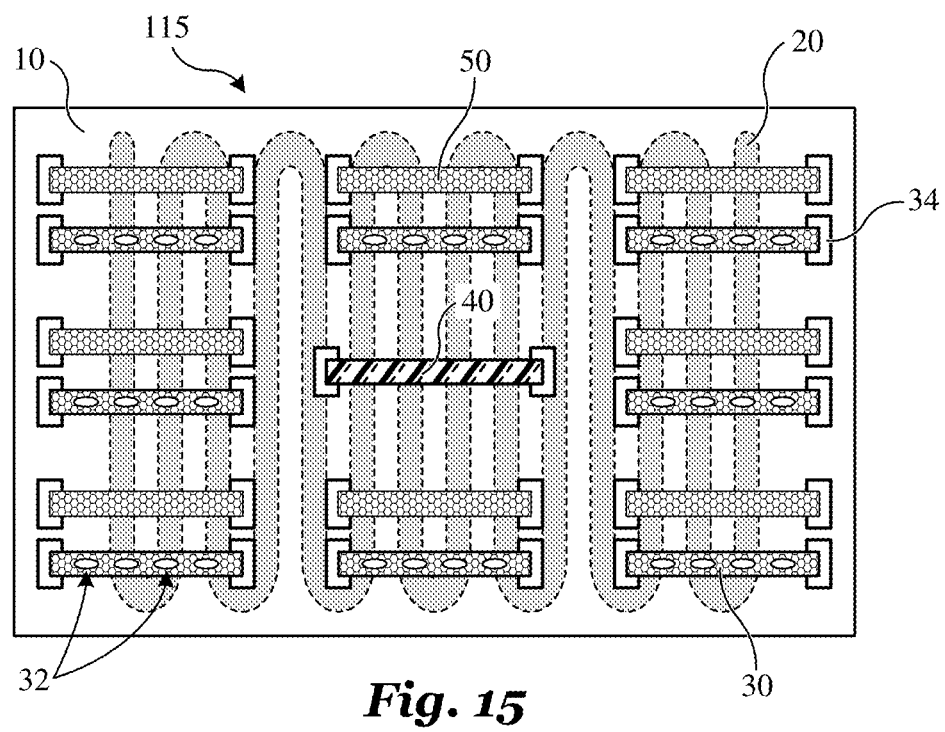
FIG. 15 illustrates a top view of an example sensor device including multiple pairs of a sensor and a reference sensor and further including an environmental sensor in accordance with an embodiment of the invention.

FIG. 15 illustrates a top view of an example sensor device including multiple pairs of a sensor and a reference sensor and further including an environmental sensor in accordance with an embodiment of the invention.

Referring to FIG. 15, a sensor device 115 includes multiple pairs of sensor 30 and a structural reference sensor 50 arranged in an array on a substrate 10 and a heating element in or within substrate 10 as previously described. In contrast to sensor device 114, sensor device 115 also includes an environmental sensor 40 centrally located on substrate 10. The environmental sensor 40 may be used as a reference for correcting the baseline variation of sensors 30 in addition to the structural reference sensors 50.

Figure 16:
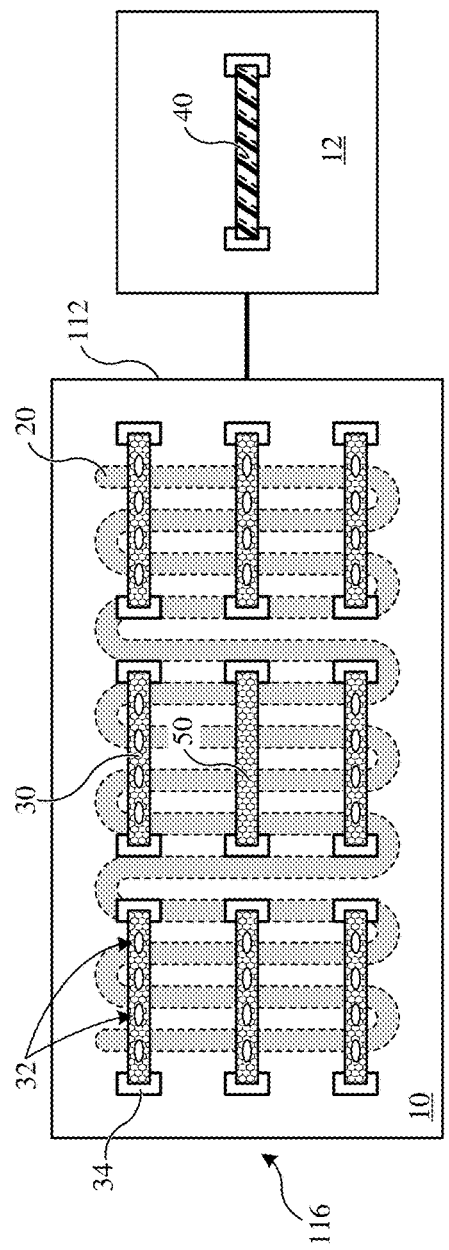
FIG. 16 illustrates a top view of an example sensor device including multiple sensors, an environmental sensor, and a reference sensor where the environmental sensor is located on a second substrate in accordance with an embodiment of the invention.
Figure 17:
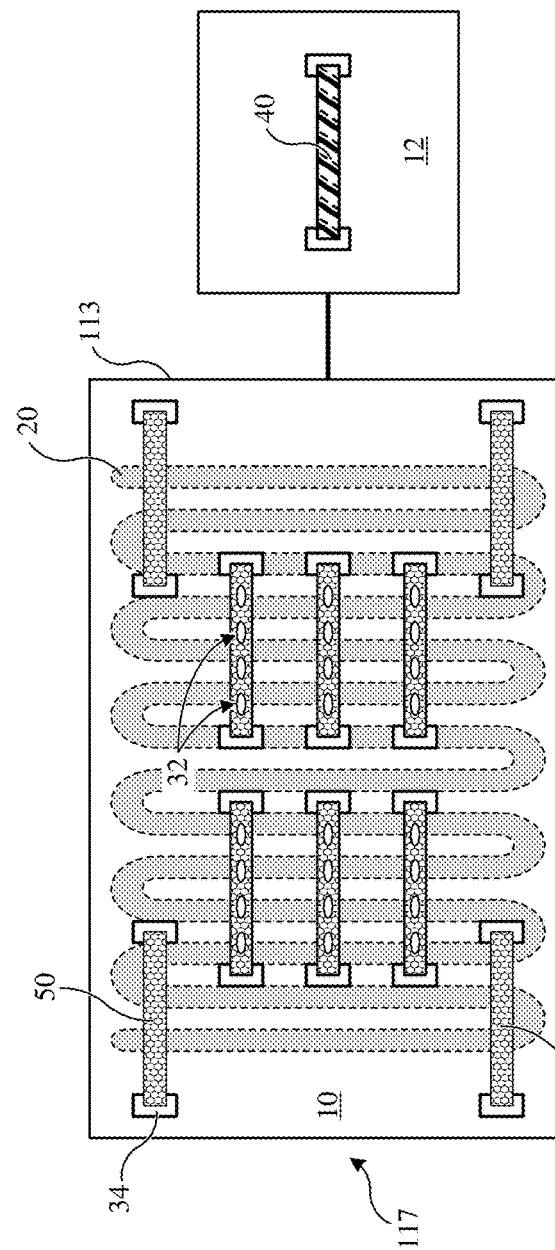
FIG. 17 illustrates a top view of an example sensor device including multiple sensors, and environmental sensor, and multiple reference sensors where the environmental sensor is located on a second substrate in accordance with an embodiment of the invention.

FIGS. 16, 17, and 18 illustrate top views of example sensor devices including multiple sensors, and an environmental sensor where the environmental sensor is located on a second substrate in accordance with embodiments of the invention. FIG. 16 illustrates an example sensor device that includes a single reference sensor, FIG. 17 illustrates an example sensor device that includes multiple reference sensors, and FIG. 18 illustrates an example sensor device that includes multiple pairs of a sensor and a reference sensor.

Referring to FIG. 16, a sensor device 116 includes a sensor device 112 as previously described in reference to FIG. 12 operatively coupled to a second substrate 12. An environmental sensor 40 is attached to the second substrate 12.

Referring now to FIG. 17, a sensor device 117 includes a sensor device 113 as previously described in reference to FIG. 13 operatively coupled to a second substrate 12. An environmental sensor 40 is attached to the second substrate 12.

Referring now to FIG. 18, a sensor device 118 includes a sensor device 114 as previously described in reference to FIG. 14 operatively coupled to a second substrate 12. An environmental sensor 40 is attached to the second substrate 12.

In any of the previous embodiments, additional environmental sensors may also be included. Additional types of environmental sensors may also be included as described in an example in reference to FIG. 4. Multiple types of sensors may also be included on the same substrate or in the same sensor device, sensor package, or sensing system. The invention is also not limited to the correcting the baseline variation of sensors, but may also be applied to any device that is significantly affected by environmental factors.

Figure 19A:
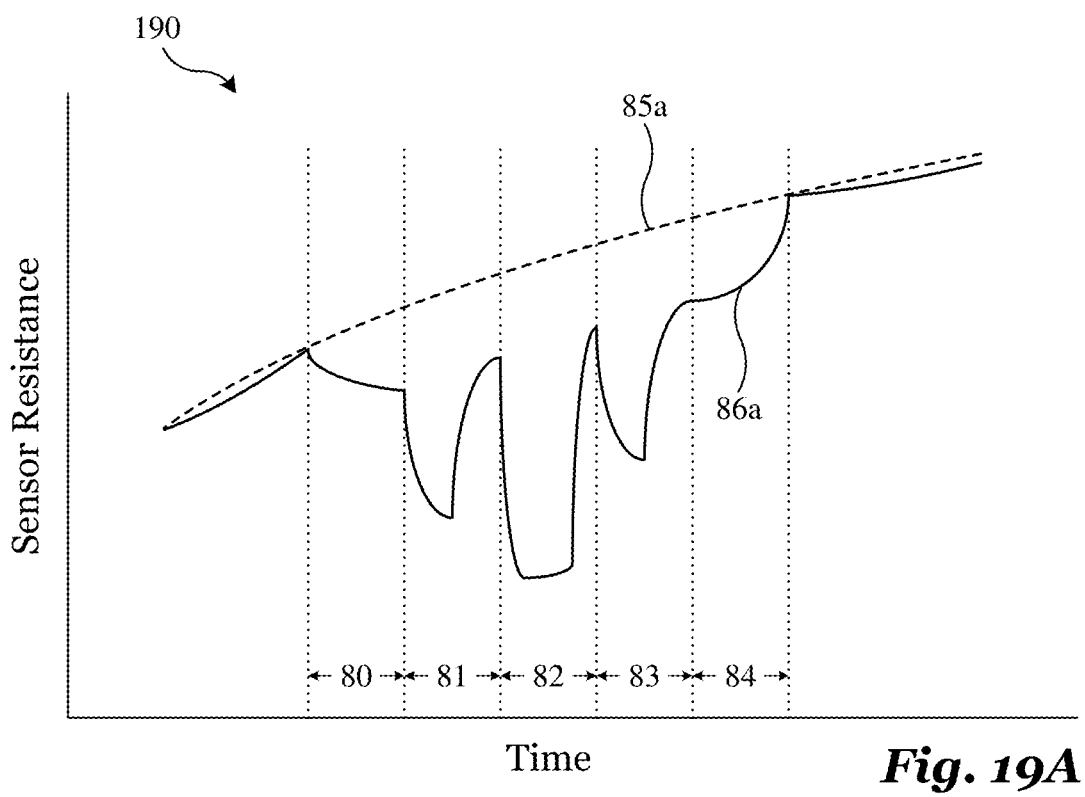
FIGS. 19A and 19B illustrate qualitative graphs of sensor resistance versus time and heating element resistance versus time with baseline variation due to sensor drift where
Figure 19B:
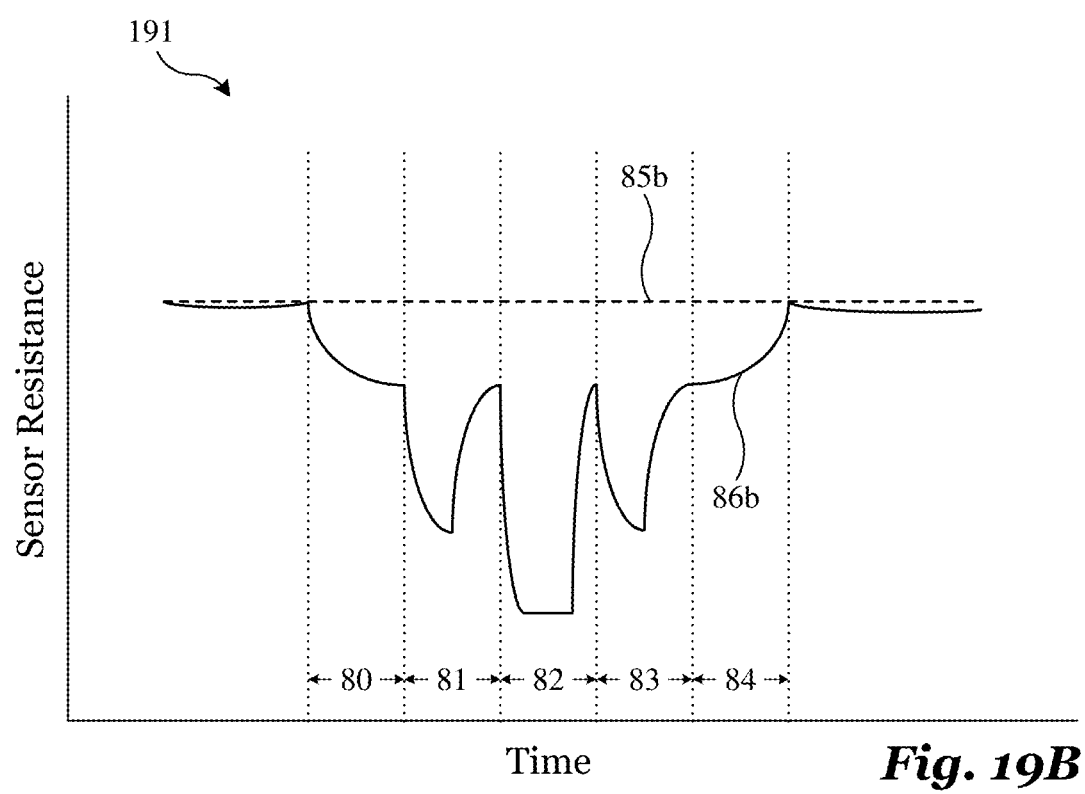

FIGS. 19A and 19B illustrate qualitative graphs of sensor resistance versus time and heating element resistance versus time with baseline variation due to sensor drift where FIG. 19A illustrates resistance responses of a sensor and a heating element before correcting the baseline variation and FIG. 19B illustrates resistance responses of the sensor and the heating element after correcting the baseline variation.

Referring to FIG. 19A, graph 190 shows a heating element resistance curve 85a and a sensor resistance curve 86a as a function of time. Heating element resistance 85a may be considered an indication of a variable baseline, as can be seen by the gradual increase in heater resistance over time. Sensor resistance curve 86a is also shown to follow this trend of increasing resistance which may indicate a correlation between the response of the heating element and the response of the sensor.

Now referring to FIG. 19B, the correlation between the response of the heating element and the response of the sensor have been used to correct for baseline variation and generate corrected heating element resistance curve 85b and corrected sensor resistance curve 86b as shown in graph 191. Notably, corrected heating element resistance curve 85b is constant in time.

Sensor resistance curve 86a and corrected sensor resistance curve 86b are shown to have a feature in each of five time intervals: first time interval 80, second time interval 81, third time interval 82, fourth time interval 83, and fifth time interval 84. In this specific example, a small concentration of a target analyte is detected in first time interval 80 and fifth time interval 85, a medium concentration of a target analyte is detected in second time interval 81 and fourth time interval 83, and a large concentration of a target analyte is detected in third time interval 82. For corrected sensor response 86b, the respective features of the five time intervals are now advantageously measured from a constant baseline.

Figure 20A:
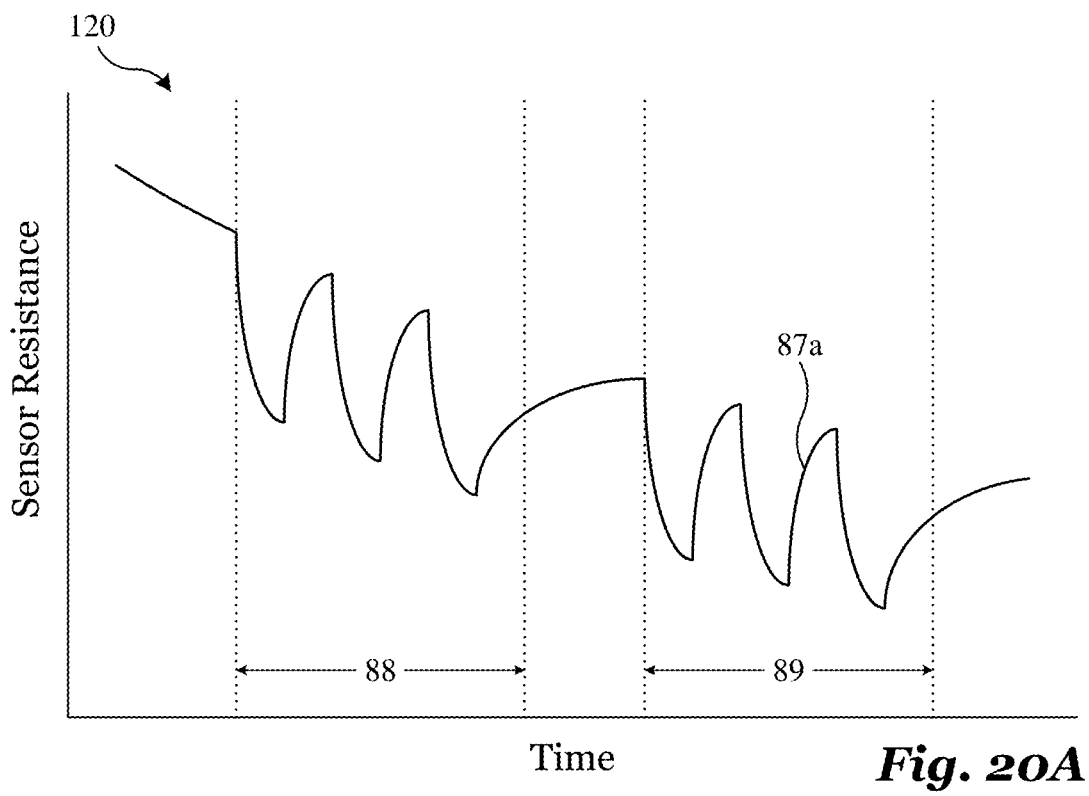
FIGS. 20A and 20B illustrate qualitative graphs of sensor resistance versus time with baseline variation due to sensor drift over multiple correction intervals where
Figure 20B:
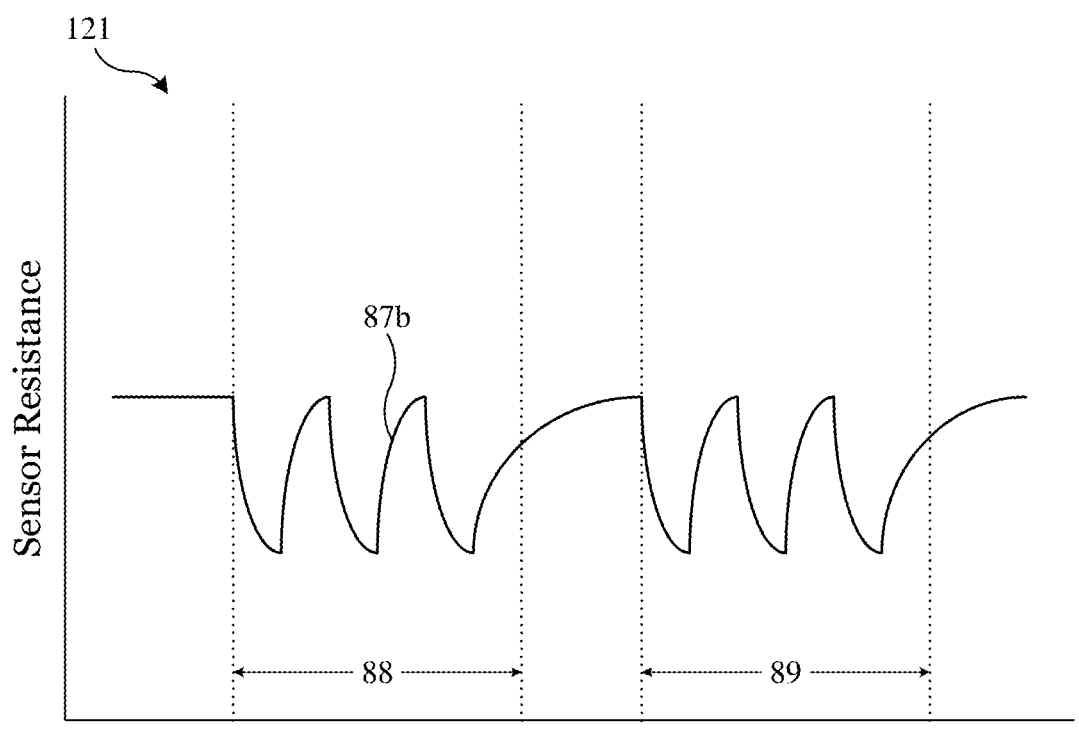

FIGS. 20A and 20B illustrate qualitative graphs of sensor resistance versus time with baseline variation due to sensor drift over multiple correction intervals where FIG. 20A illustrates resistance responses of a sensor before correcting the baseline variation and FIG. 20B illustrates resistance responses of the sensor after correcting the baseline variation.

Referring to FIGS. 20A and 20B, graph 120 shows a sensor resistance curve 87a subject to baseline variation with a first correction interval 88 and a second correction interval 89. Graph 121 shows a corrected sensor resistance curve 87b where the baseline is now constant. In this embodiment, a correlation is determined between the sensor and a reference prior to first correction interval 88 and then used to correct the sensor resistance during first correction interval 88. After first correction time interval 88, a correlation is again determined between the sensor and the reference and used to correct the sensor resistance during the second correction interval 89. This may continue to be repeated as has been described in further detail in previous embodiments.

Example embodiments of the present invention are summarized here. Other embodiments can also be understood from the entirety of the specification as well as the claims filed herein.

Example 1

A method of sensing, the method including: obtaining, by a sensor, first sensor data points; obtaining first reference data points; determining a correlation between the first sensor data points and the first reference data points; measuring, by the sensor, second sensor data points; obtaining second reference data points; adjusting the second sensor data points using the correlation and the second reference data points to obtain corrected sensor data points; determining sensed values from the corrected sensor data points; and storing the sensed values.

Example 2

The method of example 1, where the sensor is a resistive gas sensor.

Example 3

The method of one of examples 1 and 2, where the sensor includes graphene.

Example 4

The method of one of examples 1 to 3, where determining the correlation includes determining a plurality of correlation coefficients using regression analysis.

Example 5

The method of one of examples 1 to 4, where adjusting the second sensor data points includes using the correlation to determine instantaneous baseline values for each of the second sensor data points, and subtracting the instantaneous baseline values from the corresponding second sensor data points.

Example 6

The method of one of examples 1 to 5, further including: normalizing the corrected sensor data points before determining the sensed values.

Example 7

The method of one of examples 1 to 6, where obtaining the first reference points and obtaining the second reference points includes obtaining resistance values of a heating element.

Example 8

The method of one of examples 1 to 6, where obtaining the first reference points and obtaining the second reference points includes obtaining ambient temperature measurements from a temperature sensor.

Example 9

A method of sensing, the method including: obtaining, by a sensor, first sensor data points during a first time interval; obtaining first reference data points during the first time interval; and during a second time interval and after the first time interval, measuring, by the sensor, second sensor data points, generating corrected second sensor data points by correcting for baseline variation in the second sensor data points using a relationship between the first sensor data points and the first reference data points, and determining sensed values from the corrected second sensor data points.

Example 10

The method of example 9, where the sensor is a resistive gas sensor.

Example 11

The method of one of examples 9 and 10, where the sensor includes graphene.

Example 12

The method of one of examples 9 to 11, further including: after an expiration of the second time interval and during a third time interval, obtaining, by a sensor, third sensor data points; obtaining third reference data points during the third time interval; and during a fourth time interval and after the third time interval, repeating the steps of measuring, by the sensor, fourth sensor data points, generating corrected fourth sensor data points be correcting for baseline variation in the fourth sensor data points using a relationship between the third sensor data points and the third reference data points, and determining second sensed values from the corrected fourth sensor data points.

Example 13

The method of one of examples 9 to 11, further including: during the second time interval, obtaining second reference data points; and during a third time interval and after the third time interval, obtaining, by the sensor, third sensor data points, generating corrected third sensor data points by correcting for baseline variation in the third sensor data points using a relationship between the second sensor data points and the second reference data points, and determining sensed values from the corrected third sensor data points.

Example 14

The method of one of examples 9 to 13, where obtaining the first reference points includes obtaining resistance values of a heating element.

Example 15

A sensor device including: a gas sensor disposed on a first substrate, the gas sensor being configured to measure first sensor data points and second sensor data points; a heating element disposed within the first substrate, where the gas sensor overlaps the heating element; a processor operatively coupled to the gas sensor and the heating element; and a memory storing a program to be executed by the processor, the program including instructions for recording first resistance values and second resistance values of the heating element, adjusting the second sensor data points using the first sensor data points, the first resistance values, and the second resistance values to obtain corrected sensor data points, and determining sensed values from the corrected sensor data points.

Example 16

The sensor device of example 15, where the gas sensor includes graphene.

Example 17

The sensor device of one of examples 15 and 16, where the gas sensor is a resistive gas sensor.

Example 18

The sensor device of one of examples 15 and 16, where the gas sensor is a capacitive gas sensor.

Example 19

The sensor device of one of examples 15 to 18, further including: a reference sensor disposed on the substrate and adjacent to the gas sensor, the reference sensor being configured to measure first reference sensor data points and second reference sensor data points, where the program includes further instructions for using the first reference sensor data points and the second reference sensor data points when adjusting the second sensor data points.

Example 20

The sensor device of one of examples 15 to 19, further including: an environmental sensor disposed on a second substrate operatively coupled to the first substrate, the environmental sensor configured to measure first environmental data points and second environmental data points, where the program includes further instructions for using the first environmental data points and the second environmental data points when adjusting the second sensor data points.

Example 21

The sensor device of example 20, where the environmental sensor is a humidity sensor.

Example 22

The sensor device of one of examples 20 and 21, where the processor is an application-specific integrated circuit (ASIC) and is disposed on the second substrate.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A sensor device comprising:
a gas sensor disposed on a substrate, the gas sensor being configured to measure first sensor data points and second sensor data points;
a reference sensor disposed on the substrate and adjacent to the gas sensor, the reference sensor being configured to measure first reference sensor data points and second reference sensor data points;
a processor operatively coupled to the gas sensor and the reference sensor; and
a memory storing a program to be executed by the processor, the program comprising instructions for performing the following steps in real-time,
determining a correlation between the first sensor data points and the first reference sensor data points by performing real-time regression analysis, the correlation comprising a set of correlation coefficients obtained from the real-time regression analysis,
adjusting the second sensor data points using the correlation and the second reference sensor data points to obtain corrected sensor data points, and
determining sensed values from the corrected sensor data points.

2. The sensor device of claim 1, further comprising:
a heating element disposed within the substrate, wherein the gas sensor overlaps the heating element, and wherein the program comprises further instructions for recording first resistance values and second resistance values of the heating element, and
using the first resistance values and the second resistance values when adjusting the second sensor data points.

3. The sensor device of claim 1, wherein the gas sensor comprises graphene.

4. The sensor device of claim 1, wherein the gas sensor is a resistive gas sensor.

5. The sensor device of claim 1, further comprising:
an environmental sensor operatively coupled to the substrate, the environmental sensor configured to measure first environmental data points and second environmental data points, wherein the program comprises further instructions for using the first environmental data points and the second environmental data points when adjusting the second sensor data points.

6. The sensor device of claim 1, wherein the reference sensor is a temperature sensor.

7. The sensor device of claim 1, wherein the reference sensor is a structural reference sensor comprising a similar structure as the gas sensor.

8. A sensor device comprising:
a gas sensor disposed on a substrate, the gas sensor being configured to measure first sensor data points and second sensor data points;
a reference sensor disposed on the substrate and adjacent to the gas sensor, the reference sensor being configured to measure first reference sensor data points and second reference sensor data points;
a processor operatively coupled to the gas sensor and the reference sensor; and
a memory storing a program to be executed by the processor, the program comprising instructions for,
determining, in real-time, a correlation between the first sensor data points and the first reference sensor data points by performing real-time regression analysis, the correlation comprising a set of correlation coefficients obtained from the real-time regression analysis,
determining instantaneous baseline values for each of the second sensor data points using the correlation,
subtracting the instantaneous baseline values from the corresponding second sensor data points to obtain corrected sensor data points, and
determining sensed values from the corrected sensor data points.

9. The sensor device of claim 8, further comprising:
a heating element disposed within the substrate, wherein the gas sensor overlaps the heating element, and wherein the program comprises further instructions for
recording first resistance values and second resistance values of the heating element, and
using the first resistance values and the second resistance values when determining the instantaneous baseline values.

10. The sensor device of claim 8, wherein the gas sensor comprises graphene.

11. The sensor device of claim 8, wherein the gas sensor is a resistive gas sensor.

12. The sensor device of claim 8, wherein the reference sensor is a temperature sensor.

13. The sensor device of claim 8, wherein the reference sensor is a structural reference sensor comprising a similar structure as the gas sensor.

14. A sensor device comprising:
a processor configured to be operatively coupled to a gas sensor and a reference sensor; and
a memory storing a program to be executed by the processor, the program comprising instructions for performing the following steps in real-time,
receiving first sensor data points and second sensor data points measured by the gas sensor,
receiving first reference sensor data points and second reference sensor data points measured by the reference sensor,
determining a correlation between the first sensor data points and the first reference sensor data points by performing real-time regression analysis, the correlation comprising a set of correlation coefficients obtained from the real-time regression analysis,
adjusting the second sensor data points using the correlation and the second reference sensor data points to obtain corrected sensor data points, and
determining sensed values from the corrected sensor data points.

15. The sensor device of claim 14,
wherein the processor is further configured to be operatively coupled to an environmental sensor, the environmental sensor being configured to measure first environmental data points and second environmental data points, and
wherein the program comprises further instructions for using the first environmental data points and the second environmental data points when adjusting the second sensor data points.

16. The sensor device of claim 14, wherein adjusting the second sensor data points using the correlation and the second reference sensor data points to obtain the corrected sensor data points comprises
determining instantaneous baseline values for each of the second sensor data points using the correlation, and
subtracting the instantaneous baseline values from the corresponding second sensor data points to obtain the corrected sensor data points.

17. The sensor device of claim 14, further comprising:
a substrate supporting the gas sensor; and
a heating element disposed within the substrate, the gas sensor overlapping the heating element, wherein the program comprises further instructions for
recording first resistance values and second resistance values of the heating element, and
using the first resistance values and the second resistance values when adjusting the second sensor data points.

18. The sensor device of claim 17, wherein the gas sensor comprises graphene.

19. The sensor device of claim 18, wherein the reference sensor is a structural reference sensor comprising graphene.

20. The sensor device of claim 17, wherein the gas sensor is a resistive gas sensor.

* * * * *